US009982317B2

(12) United States Patent
McDonald et al.

(10) Patent No.: US 9,982,317 B2
(45) Date of Patent: May 29, 2018

(54) SYSTEMS AND METHODS FOR ACID RECYCLE

(75) Inventors: William F. McDonald, Utica, OH (US); Shannon Scott Urban, Valley Springs, SD (US); Jason L. Martin, Sioux Falls, SD (US)

(73) Assignee: Poet Research, Inc., Sioux Falls, SD (US)

( * ) Notice: Subject to any disclaimer, the term of this patent is extended or adjusted under 35 U.S.C. 154(b) by 46 days.

(21) Appl. No.: 14/130,878

(22) PCT Filed: Jul. 9, 2012

(86) PCT No.: PCT/US2012/045953
§ 371 (c)(1),
(2), (4) Date: Mar. 5, 2014

(87) PCT Pub. No.: WO2013/006856
PCT Pub. Date: Jan. 10, 2013

(65) Prior Publication Data
US 2014/0209092 A1    Jul. 31, 2014

Related U.S. Application Data

(60) Provisional application No. 61/505,389, filed on Jul. 7, 2011.

(51) Int. Cl.
*C13K 13/00*    (2006.01)
*C13K 1/02*    (2006.01)

(52) U.S. Cl.
CPC .............. *C13K 13/002* (2013.01); *C13K 1/02* (2013.01); *C13K 13/007* (2013.01);
(Continued)

(58) Field of Classification Search
CPC .................................................. C13K 13/002
See application file for complete search history.

(56) References Cited

U.S. PATENT DOCUMENTS 2,734,836 A    2/1956 Elian et al.
3,212,932 A    10/1965 Hess et al.
(Continued)

FOREIGN PATENT DOCUMENTS

DE    222 636 A1    5/1985
EP    0 044 658    1/1982
(Continued)

OTHER PUBLICATIONS

Adney, B. et al., "Measurement of Cellulase Activities", Technical Report NREL/TP-510-42628 (2008) Cover; p. 1-8.
(Continued)

*Primary Examiner* — Douglas B Call
(74) *Attorney, Agent, or Firm* — Kagan Binder, PLLC

(57) ABSTRACT

Methods and systems for pretreating lignocellulosic biomass are disclosed. An acid solution between 1% to 1.6% sulfuric acid is applied to the biomass. The biomass is subjected to an elevated temperature to cause the production of xylose, glucose, and furfural. Adjustments to temperature, acid concentration, and time can generate at least 80% or 90% of theoretical xylose, 45% or 50% of the theoretical glucose, and less than 4000 ppm of furfural in the xylose liquor. A portion of the resulting xylose liquor may be separated from the glucan solids. The xylose liquor, still highly acidic, can be recycled to reduce subsequent acid loading requirements. Makeup acid solution is added to the xylose liquor and subsequent biomass to ensure a proper solids to liquids ratio. The biomass is again treated to higher temperatures to yield sugars. The process may be repeated for each subsequent cycle.

11 Claims, 18 Drawing Sheets

(52) U.S. Cl.
CPC ...... *C12P 2201/00* (2013.01); *C12P 2203/00* (2013.01); *Y02E 50/16* (2013.01)

(56) References Cited

U.S. PATENT DOCUMENTS

| | | | |
|---|---|---|---|
| 4,014,743 A | 3/1977 | Black | |
| 4,029,515 A | 6/1977 | Kiminki et al. | |
| 4,072,538 A | 2/1978 | Fahn et al. | |
| 4,152,197 A | 5/1979 | Lindahl et al. | |
| 4,168,988 A | 9/1979 | Riehm et al. | |
| 4,342,831 A | 8/1982 | Faber et al. | |
| 4,425,433 A | 1/1984 | Neves | |
| 4,427,453 A | 1/1984 | Reitter | |
| 4,432,805 A | 2/1984 | Nuuttila et al. | |
| 4,461,648 A | 7/1984 | Foody | |
| 4,529,699 A | 7/1985 | Gerez et al. | |
| 4,552,616 A | 11/1985 | Kauppi | |
| 4,612,286 A | 9/1986 | Sherman et al. | |
| 4,668,340 A | 5/1987 | Sherman | |
| 4,752,579 A | 6/1988 | Arena et al. | |
| 4,908,098 A | 3/1990 | DeLong et al. | |
| 4,941,944 A | 7/1990 | Chang | |
| 4,997,488 A | 3/1991 | Gould et al. | |
| 5,125,977 A * | 6/1992 | Grohmann | C13K 13/002 127/36 |
| 5,171,592 A | 12/1992 | Holtzapple et al. | |
| 5,188,673 A | 2/1993 | Clausen et al. | |
| 5,221,357 A | 6/1993 | Brink | |
| 5,328,562 A | 7/1994 | Rafferty et al. | |
| 5,338,366 A | 8/1994 | Grace et al. | |
| 5,366,558 A | 11/1994 | Brink | |
| 5,370,999 A | 12/1994 | Stuart | |
| 5,411,594 A * | 5/1995 | Brelsford | B01J 19/242 127/1 |
| 5,424,417 A | 6/1995 | Torget et al. | |
| 5,498,766 A | 3/1996 | Stuart et al. | |
| 5,536,325 A | 7/1996 | Brink | |
| 5,562,777 A | 10/1996 | Farone et al. | |
| 5,580,389 A | 12/1996 | Farone et al. | |
| 5,597,714 A | 1/1997 | Farone et al. | |
| 5,628,830 A | 5/1997 | Brink | |
| 5,693,296 A | 12/1997 | Holtzapple et al. | |
| 5,705,369 A | 1/1998 | Torget et al. | |
| 5,711,817 A | 1/1998 | Titmas | |
| 5,726,046 A | 3/1998 | Farone et al. | |
| 5,733,758 A | 3/1998 | Nguyen | |
| 5,769,934 A | 6/1998 | Ha et al. | |
| 5,782,982 A | 7/1998 | Farone et al. | |
| 5,820,687 A | 10/1998 | Farone et al. | |
| 5,865,898 A | 2/1999 | Holtzapple et al. | |
| 5,879,463 A | 3/1999 | Proenca | |
| 5,916,780 A | 6/1999 | Foody et al. | |
| 5,932,452 A | 8/1999 | Mustranta et al. | |
| 5,932,456 A | 8/1999 | Van Draanen et al. | |
| 5,972,118 A | 10/1999 | Hester et al. | |
| 5,972,415 A | 10/1999 | Brassart et al. | |
| 5,975,439 A | 11/1999 | Chieffalo et al. | |
| 6,007,636 A | 12/1999 | Lightner | |
| 6,022,419 A * | 2/2000 | Torget | C07G 17/00 127/1 |
| 6,090,595 A | 7/2000 | Foody et al. | |
| 6,228,177 B1 | 5/2001 | Torget | |
| 6,379,504 B1 | 4/2002 | Miele et al. | |
| 6,419,788 B1 | 7/2002 | Wingerson | |
| 6,423,145 B1 | 7/2002 | Nguyen et al. | |
| 6,512,110 B1 | 1/2003 | Heikkila et al. | |
| 6,555,350 B2 | 4/2003 | Ahring et al. | |
| 6,569,289 B2 | 5/2003 | Stromberg et al. | |
| 6,620,292 B2 | 9/2003 | Wingerson | |
| 6,660,506 B2 | 12/2003 | Nguyen et al. | |
| 6,692,578 B2 | 2/2004 | Schmidt et al. | |
| 6,770,168 B1 | 8/2004 | Stigsson | |
| 7,198,925 B2 | 4/2007 | Foody | |
| 7,238,242 B2 | 7/2007 | Pinatti et al. | |
| 7,354,743 B2 | 4/2008 | Vlasenko et al. | |
| 7,455,997 B2 | 11/2008 | Hughes | |
| 7,501,025 B2 | 3/2009 | Bakker et al. | |
| 7,503,981 B2 | 3/2009 | Wyman et al. | |
| 7,585,652 B2 | 9/2009 | Foody et al. | |
| 7,604,967 B2 | 10/2009 | Yang et al. | |
| 7,649,086 B2 | 1/2010 | Belanger et al. | |
| 7,666,637 B2 | 2/2010 | Nguyen | |
| 7,670,813 B2 | 3/2010 | Foody et al. | |
| 7,709,042 B2 | 5/2010 | Foody et al. | |
| 7,754,456 B2 | 7/2010 | Penttila et al. | |
| 7,754,457 B2 | 7/2010 | Foody et al. | |
| 7,807,419 B2 | 10/2010 | Hennessey et al. | |
| 7,815,741 B2 | 10/2010 | Olson | |
| 7,815,876 B2 | 10/2010 | Olson | |
| 7,819,976 B2 | 10/2010 | Friend et al. | |
| 7,875,444 B2 | 1/2011 | Yang et al. | |
| 7,901,511 B2 | 3/2011 | Griffin et al. | |
| 8,057,639 B2 | 11/2011 | Pschorn et al. | |
| 8,057,641 B2 | 11/2011 | Bartek et al. | |
| 8,123,864 B2 | 2/2012 | Christensen et al. | |
| 8,288,600 B2 | 10/2012 | Bartek et al. | |
| 8,449,728 B2 | 5/2013 | Redford | |
| 8,815,552 B2 | 8/2014 | Narendranath et al. | |
| 9,034,620 B2 | 5/2015 | Narendranath | |
| 2002/0192774 A1 | 12/2002 | Ahring et al. | |
| 2003/0199049 A1 * | 10/2003 | Nguyen | C12P 7/08 435/165 |
| 2004/0060673 A1 | 4/2004 | Phillips et al. | |
| 2005/0069998 A1 | 3/2005 | Ballesteros Perdices et al. | |
| 2006/0251764 A1 | 11/2006 | Abbas et al. | |
| 2006/0281157 A1 | 12/2006 | Chotani et al. | |
| 2007/0238155 A1 | 10/2007 | Gusakov et al. | |
| 2008/0026431 A1 | 1/2008 | Saito et al. | |
| 2008/0184709 A1 | 8/2008 | Rowell | |
| 2008/0277082 A1 | 11/2008 | Pschorn et al. | |
| 2008/0295981 A1 | 12/2008 | Shin et al. | |
| 2009/0053793 A1 | 2/2009 | Lefebvre et al. | |
| 2009/0308383 A1 | 12/2009 | Shin et al. | |
| 2010/0003733 A1 | 1/2010 | Foody et al. | |
| 2010/0144001 A1 | 6/2010 | Horton | |
| 2010/0233771 A1 | 9/2010 | McDonald et al. | |
| 2010/0285553 A1 | 11/2010 | Delmas et al. | |
| 2011/0065159 A1 * | 3/2011 | Raines | C08B 1/003 435/163 |
| 2011/0079219 A1 | 4/2011 | McDonald et al. | |
| 2011/0094505 A1 | 4/2011 | Bulla et al. | |
| 2011/0171708 A1 | 7/2011 | Larsen | |
| 2012/0111514 A1 * | 5/2012 | Dottori | C13K 1/02 162/68 |
| 2012/0116063 A1 * | 5/2012 | Jansen | C08H 8/00 530/507 |
| 2012/0129234 A1 | 5/2012 | McDonald et al. | |
| 2012/0138246 A1 | 6/2012 | Christensen et al. | |
| 2012/0201947 A1 | 8/2012 | Stuart | |
| 2012/0291716 A1 * | 11/2012 | Kilambi et al. | 127/44 |
| 2013/0065289 A1 | 3/2013 | Carlson | |
| 2013/0337521 A1 | 12/2013 | Carlson et al. | |
| 2014/0024826 A1 | 1/2014 | Narendranath et al. | |
| 2014/0093920 A1 * | 4/2014 | Zhang | C08H 8/00 435/105 |
| 2014/0234911 A1 | 8/2014 | Narendranath et al. | |
| 2015/0037859 A1 | 2/2015 | Bootsma | |
| 2015/0072390 A1 | 3/2015 | Narendranath et al. | |
| 2015/0128932 A1 | 5/2015 | Kwiatkowski et al. | |

FOREIGN PATENT DOCUMENTS

| | | |
|---|---|---|
| EP | 0 098 490 | 1/1984 |
| EP | 0 159 795 | 10/1985 |
| EP | 0 884 391 | 12/1998 |
| EP | 1 259 466 | 11/2002 |
| FR | 2 397 486 | 2/1979 |
| FR | 2 609 046 | 7/1988 |
| WO | WO 92/07098 | 4/1992 |
| WO | WO 1992/007098 | 4/1992 |
| WO | WO 94/08027 | 4/1994 |
| WO | WO 94/29475 | 12/1994 |
| WO | WO 95/08648 | 3/1995 |

(56) References Cited

FOREIGN PATENT DOCUMENTS

| | | |
|---|---|---|
| WO | WO 98/14270 | 4/1998 |
| WO | WO 98/56958 | 12/1998 |
| WO | WO 99/06133 | 2/1999 |
| WO | WO 00/14120 | 3/2000 |
| WO | WO 00/61858 | 10/2000 |
| WO | WO 00/073221 | 12/2000 |
| WO | WO 01/32715 | 5/2001 |
| WO | WO 01/60752 | 8/2001 |
| WO | WO 02/14598 | 2/2002 |
| WO | WO 02/24882 | 3/2002 |
| WO | WO 02/38786 | 5/2002 |
| WO | WO 02/051561 | 7/2002 |
| WO | WO 02/067691 | 9/2002 |
| WO | WO 02/070753 | 9/2002 |
| WO | WO 03/013714 | 2/2003 |
| WO | WO 03/071025 | 8/2003 |
| WO | WO 03/078644 | 9/2003 |
| WO | WO 2005/099854 | 10/2005 |
| WO | WO 2006/032282 | 3/2006 |
| WO | WO 2006/034590 | 4/2006 |
| WO | WO 2006/056838 | 6/2006 |
| WO | WO 2007/009463 | 1/2007 |
| WO | WO 2008/095098 | 8/2008 |
| WO | WO 2008/131229 | 10/2008 |
| WO | WO 2009/045651 | 4/2009 |
| WO | WO 2009/108773 | 9/2009 |
| WO | WO 2010/102060 | 9/2010 |
| WO | WO 2010/113129 | 10/2010 |
| WO | WO 2010/113130 | 10/2010 |
| WO | WO 2011/116317 | 9/2011 |
| WO | WO 2011/159915 | 12/2011 |
| WO | WO 2012/042497 | 4/2012 |
| WO | WO 2012/042498 | 4/2012 |
| WO | WO 2012/103281 | 8/2012 |
| WO | WO 2012/131665 | 10/2012 |
| WO | WO 2012/168410 | * 12/2012 |

OTHER PUBLICATIONS

Caparros, S. et al., "Xylooligosaccharides Production from Arundo donax", J. Agric. Food Chem. 55 (2007): p. 5536-5543.
Cort, J. et al., "Minimize Scale-Up Risk", www.aiche.org/cep, (2010): p. 39-49.
Demain, A.L. et al., "Cellulase, Clostridia, and Ethanol", Microbiology and Molecular Biology Reviews 69(1) (2005): p. 124-154.
Dien, B.S. et al., "Enzyme characterization for hydrolysis of AFEX and liquid hot-water pretreated distillers' grains and their conversion to ethanol", Bioresource Technology 99 (2008): p. 5216-5225.
Gibbons, W.R. et al., "Fuel Ethanol and High Protein Feed from Corn and Corn-Whey Mixtures in a Farm-Scale Plant", Biotechnology and Bioengineering XXV (1983): p. 2127-2148.
Goodman, B. J., "FY 1988 Ethanol from Biomass Annual Report" (1989): p. 1-458.
Grohmann, K. et al., "Optimization of Dilute Acid Pretreatment of Biomass", Biotechnology and Bioengineering Symp. 15 (1985): p. 59-80.
Grohmann, K. et al., "Dilute Acid Pretreatment of Biomass at High Solids Concentrations", Biotechnology and Bioengineering Symp. 17 (1986): p. 135-151.
Humbird, D. et al., "Process Design and Economics for Biochemical Conversion of Lignocellulosic Biomass to Ethanol: Dilute-Acid Pretreatment and Enzymatic Hydrolysis of Corn Stover", National Renewable Energy Laboratory (2011): Covers with Introduction; p. 1-114.
Jeoh, T. "Steam Explosion Pretreatment of Cotton Gin Waste for Fuel Ethanol Production", Thesis submitted to Virginia Polytechnic Institute and State University (1998): Cover with Introduction; p. 1-138.
Jorgensen, H. et al., "Enzymatic conversion of lignocellulose into fermentable sugars: challenges and opportunities", Biofuels, Bioprod. Bioref. 1 (2001): p. 119-134.

Kumar, R. et al., "Effect of Enzyme Supplementation at Moderate Cellulase Loadings on Initial Glucose and Xylose Release from Corn Stover Solids Pretreated by Leading Technologies", Biotechnology and Bioengineering 102(2) (2009): p. 457-467.
Larsen, J. et al., "The IBUS Process—Lignocellulosic Bioethanol Close to a Commercial Reality", Chem. Eng. Technol. 31(5) (2008): p. 765-772.
Lynd, L.R. et al. "Consolidated bioprocessing of cellulosic biomass: an update", Current Opinion in Biotechnology 16 (2005): p. 577-583.
Mosier, N. et al., "Features of promising technologies for pretreatment of lignocellulosic biomass", Bioresource Technology 96 (2005): p. 673-686.
McMillan, J.D. "Processes for Pretreating Lignocellulosic Biomass: A Review", National Renewable Energy Laboratory (1992): Covers with Introduction; p. 1-44.
Nandini, C. et al. "Carbohydrate composition of wheat, wheat bran, sorghum and bajra with good chapatti/roti (Indian flat bread) making quality", Food Chemistry 73 (2001): p. 197-203.
Sanchez, O.J. et al., "Trends in biotechnological production of fuel ethanol from different feedstocks", Bioresource Technology 99 (2008): p. 5270-5295.
Saska, M. et al., "Aqueous Extraction of Sugarcane Bagasse Hemicellulose and Production of Xylose Syrup", Biotechnology and Bioengineering 45 (1995): p. 517-523.
Sepulveda-Huerta, E. et al. "Production of detoxified sorghum straw hydrolysates for fermentative purposes", Journal of the Science of Food and Agriculture 86 (2006): p. 2579-2586.
Spindler, D. et al., "Evaluation of Pretreated Woody Crops for the Simultaneous Saccharification and Fermentation Process", Ethanol from Biomass. FY 1988, Annual Report (1989): p. B33-B43.
Taherzadeh, M.J. et al., "Acid-based Hydrolysis Processes for Ethanol from Lignocellulosic Materials: A Review", BioResources 2(3) (2007): p. 472-499.
Taherzadeh, M.J. et al., "Enzyme-based Hydrolysis Processes for Ethanol from Lignocellulosic Materials: A Review", BioResources 2(4) (2007): p. 707-738.
Texeira, R.H. et al., "Ethanol Annual Report FY 1990", (1991): p. 1-346.
Torget, R. et al., "Dilute Acid Pretreatment of Short Rotation Woody and Herbaceous Crops", Applied Biochemistry and Biotechnology 24/25 (1990): p. 115-126.
Torget, R. et al., "Initial Design of a Dilute Sulfuric Acid Pretreatment Process for Aspen Wood Chips", Solar Energy Research Institute (1988): p. 89-104.
Torget, R. et al., "Dilute Acid Pretreatment of Corn Cobs, Corn Stover, and Short-Rotation Crops", FY 1990 Ethanol Annual Report (1991): p. 71-82.
Weil, J. et al., "Pretreatment of Corn Fiber by Pressure Cooking in Water", Applied Biochemistry and Biotechnology 73 (1998): p. 1-17.
Wyman, Charles E., "What is (and is not) vital to advancing cellulosic ethanol", Trends in Biotechnology 25(4) (2007): p. 153-157.
Wyman, C.E. et al., "Coordinated development of leading biomass pretreatment technologies", Bioresource Technology 96 (2005): p. 1959-1966.
Yang, B. et al., "Pretreatment: the key to unlocking low-cost cellulosic ethanol", Biofuels, Bioprod. Bioref. 2 (2008): p. 26-40.
Zhang, Y-H.P. et al., "Outlook for cellulose improvement: Screening and selection strategies", Biotechnology Advances 24 (2006): p. 452-481.
Zhang, Y.P. et al., "Toward an Aggregated Understanding of Enzymatic Hydrolysis of Cellulose: Noncomplexed Cellulase Systems", Biotechnology and Bioengineering 88(7) (2004): p. 797-824.
U.S. Appl. No. 12/716,989, filed Mar. 2010, Kwiatkowski.
U.S. Appl. No. 12/827,948, filed Jun. 2010, Bootsma et al.
U.S. Appl. No. 13/209,170, filed Aug. 2011, Bly et al.
Taherzadeh, M.J. et al. "Pretreatment of Lignocellulosic Wastes to Improve Ethanol and Biogas Production: A Review", Int. J. Mol. Sci. 9 (2008): p. 1621-1651.

* cited by examiner

FIG. 20A

Biomass Composition

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
| | | | | Xylan (percent) | Arabinan (percent) | Acetate (percent) | Composite (percent) | | |
| 100 | 0 | 0 | 36.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |
| 0 | 0 | 100 | 41.7 | 22.5 | 2.4 | 2.6 | 27.5 | 18.3 | 3.7 |
| 50 | 0 | 50 | 38.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 35 | 45 | 20 | 37.7 | 27.7 | 3.9 | 2.6 | 34.2 | 14.7 | 5.0 |

FIG. 20B

Biomass Typical and Expected Composition

| | Cellulose (Glucan) (percent) (approx.) | Hemicellulose (percent) (approx.) | Lignin (percent) (approx.) | Ash (percent) (approx.) |
|---|---|---|---|---|
| Typical Range | 35-45 | 24-42 | 12-20 | 2-6 |
| Expected Range | 30-55 | 20-50 | 10-25 | 1-10 |

FIG. 21A

Pre-Treated Biomass Liquid Component Composition

| Cob (percent) | Husks/ Leaves (percent) | Stalk (percent) | Glucose (percent) | Xylose (percent) | Arabinose (percent) | Acetic Acid (ppm) |
|---|---|---|---|---|---|---|
| 100 | 0 | 0 | 0.4 | 4.9 | 0.5 | 6090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6135 |
| 35 | 45 | 20 | 0.4 | 3.7 | 0.5 | 4898 |

FIG. 21B
Pre-Treated Biomass
Liquid Component
Typical and Expected Composition

|  | Glucose (percent) (approx.) | Xylose (percent) (approx.) | Arabinose (percent) (approx.) | Acetic Acid (ppm) (approx.) |
|---|---|---|---|---|
| Typical Range | 0-1 | 2-6 | 0-1 | 3000-6400 |
| Expected Range | 0-1 | 1-8 | 0-1 | 2000-8000 |

FIG. 22A
Pre-Treated Biomass
Solids Component Composition

| Cob (percent) | Husks/Leaves (percent) | Stalk (percent) | Cellulose (Glucan) (percent) | Hemicellulose | | | | Lignin (percent) | Ash (percent) |
|---|---|---|---|---|---|---|---|---|---|
| | | | | Xylan (percent) | Arabinan (percent) | Acetate (percent) | Composite (percent) | | |
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 3.1 |
| 50 | 0 | 50 | 55.7 | 5.5 | 0.9 | 0.6 | 13.1 | 27.0 | 2.2 |
| 50 | 50 | 0 | 57.3 | 5.4 | 0.8 | 0.5 | 10.6 | 25.2 | 5.4 |
| 35 | 45 | 20 | 55.8 | 4.2 | 0.8 | 0.6 | 11.5 | 25.4 | 5.8 |

FIG. 22B
Pre-Treated Biomass
Solids Component
Typical and Expected Composition

|  | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 5-20 | 20-32 | 1-10 |

FIG. 23

Theoretical Acid/Water usage and acid cost

| kg liquor recycled/PT | 0 | 2100 | 3000 | 3600 | 4200 |
|---|---|---|---|---|---|
| kg water usage | 59400 | 38610 | 29700 | 23760 | 17820 |
| kg acid usage | 600 | 390 | 300 | 240 | 180 |
| $ cost for acid ($.13/kg) | 78 | 50.7 | 39 | 31.2 | 23.4 |
| % Reduction | 0 | 35 | 50 | 60 | 70 |

FIG. 24

Experimental conditions

| PT series ID | Temperature (°C) | Time (min) | $H_2SO_4$ Concentration (%) | # of Recycles | Saccharification Time (hour) |
|---|---|---|---|---|---|
| RB471-27 | 120 | 120 | 1 | 5 | *72 |
| RB471-29 | 130 | 60 | 1 | 9 | *NA |
| RB471-49 | 140 | 20 | 1 | 9 | 72 |
| RB471-51 | 150 | 10 | 1 | 9 | 72 |
| RB471-55 | 140 | 20 | 1.6 | 4 | 96 |
| SU483-15 | 140 | 20 | 1 | 4 | 96 |
| SU483-16 | 140 | 20 | 1.6 | 4 | 96 |
| RB471-58 | 120 | 120 | 1.2 | 4 | 96 |
| SU483-17 | 120 | 120 | 1.6 | 4 | 96 |
| SU483-18 | 120 | 120 | 1.4 | 4 | 96 |

*sacc was not performed on the RB471-29 samples. Sacc was only performed on the 0$^{th}$ and 5$^{th}$ recycles for RB471-27.

FIG. 25

Acid/water reduction, glucose yields and xylose yield possible without conversion to furfural

| PT Conditions | Mean Acid/Water % Reduction | Xylose Yield % | | Glucose Yield % | | Furfural ppm |
|---|---|---|---|---|---|---|
| Temp, Time, %H* | | Avg | Std Dev | Avg | Std Dev | max |
| 120C, 120min, 1% | 78.6 | 90.8 | 4.2 | 49.4 | 9.2 | 1817.4 |
| 120C, 120min, 1.2% | 74.8 | 93.0 | 1.3 | 49.4 | 0.8 | 2070.5 |
| 120C, 120min, 1.4% | 72.2 | 92.5 | 1.6 | 51.4 | 2.5 | 2974.8 |
| 120C, 120min, 1.6% | 75.9 | 91.2 | 5.2 | 51.4 | 2.8 | 4187.8 |
| 130C, 60min, 1% | 78.5 | 93.0 | 3.6 | NA | NA | 2393.2 |
| 140C, 20min, 1% | 82.1 | 95.6 | 4.5 | 48.9 | 3.8 | 2155.0 |
| 140C, 20min, 1% | 75.0 | 96.6 | 0.6 | 56.3 | 2.8 | 1881.8 |
| 140C, 20min, 1.6% | 61.2 | 98.2 | 1.9 | 62.7 | 5.4 | 3861.1 |
| 140C, 20min, 1.6% | 77.4 | 98.4 | 3.1 | 59.4 | 4.6 | 3677.1 |
| 150C, 10min, 1% | 77.6 | 100.4 | 2.0 | 54.7 | 4.4 | 3048.4 |

SYSTEMS AND METHODS FOR ACID RECYCLE

CROSS-REFERENCE TO RELATED APPLICATIONS

This application claims the benefit of U.S. Provisional Application Ser. No. 61/505,389, filed Jul. 7, 2011, and entitled "SYSTEMS AND METHODS FOR ACID RECYCLE", the entirety of which is expressly incorporated herein by reference.

FIELD

The subject disclosure relates to systems and methods for the recycle of acid in a xylose stream in the production of ethanol from a cellulosic feedstock. The subject disclosure also relates to systems and methods for pre-treatment of biomass before the biomass is provided to a hydrolysis system and subsequently to a fermentation system in order to facilitate the efficient production of ethanol.

BACKGROUND

Ethanol can be produced from grain-based feedstocks (e.g. corn, sorghum/milo, barley, wheat, soybeans, etc.), from sugar (e.g. from sugar cane, sugar beets, etc.), and from biomass (e.g. from cellulosic feedstocks such as switchgrass, corn cobs and stover, wood, or other plant material).

Biomass comprises plant matter that can be suitable for direct use as fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during and/or after harvesting of the corn kernels, fiber from the corn kernel, switchgrass, farm or agricultural residue, wood chips or other wood waste, and other plant matter. In order to be used or processed, biomass is harvested and collected from the field and transported to the location where it is to be used or processed.

In a biorefinery configured to produce ethanol from biomass, such as cellulosic feedstocks as indicated above, ethanol is produced from lignocellulosic material (e.g. cellulose and/or hemi-cellulose). The biomass is prepared so that sugars in the cellulosic material (such as glucose from the cellulose and xylose from the hemi-cellulose) can be accessed and fermented into a fermentation product that comprises ethanol (among other things). The fermentation product is then sent to a distillation system, where the ethanol is recovered by distillation and dehydration. Other bioproducts, such as lignin and organic acids, may also be recovered as co-products. Determination of how to more efficiently prepare and treat the biomass for production into ethanol depends upon (among other things) the form and type or composition of the biomass.

One costly step in the preparation of lignocellulosic material for fermentation is the pretreatment of the biomass material, which requires the usage of a suppressed pH in order to degrade the cellulose to sugars. Typically, large doses of acid are utilized to bring the pH of the biomass to the levels required to effectively separate C5 sugars from the C6 solids. The volume of acid required for a commercial scale cellulosic ethanol plant can be very large, which is costly to purchase and store. Further, the large quantities of acid must be subsequently neutralized prior to downstream processing, such as fermentation. Neutralization is also associated with a significant cost, and may result in an excess of minerals, which can buildup in downstream systems.

SUMMARY

The disclosed aspects relate to systems and methods for pretreating lignocellulosic biomass. The pretreated biomass may be supplied to a fermentation system, or a saccharification system followed by a fermentation system, for the generation of a fermentation product. In some embodiments, the biomass may include ground corncobs, corn stover, or a combination of ground corncobs and corn stover. In some embodiments, the fermentation product may be ethanol or other bio-fuel.

In some embodiments, a method includes applying an acid solution to a first portion of biomass. The acid solution may include between about 1% to about 1.6% sulfuric acid, in some embodiments. The biomass may be subjected to an elevated temperature for a length of time in order to yield xylose sugars in a xylose liquor and glucan solids. In some embodiments, the temperature may be maintained between about 120° C. to about 150° C. for a period of between around 10 minutes to around 120 minutes.

The elevated temperature can cause xylose, glucose, and furfural to be produced. In an aspect, at least approximately 80% of theoretical xylose is produced. In some embodiments, temperature, acid concentration, and/or time may be optimized (e.g., altered) to generate at least about 90% of theoretical xylose. In a similar manner, the conditions (e.g., temperature, acid concentration, and/or time) may be modified to ensure around 45% or more (e.g., around 50%) of the theoretical glucose is generated. Since more severe pretreatments yield greater sugar levels, in some embodiments, the severity may be controlled such that the desired sugar is generated without causing more than approximately 4000 ppm or approximately 3000 ppm of furfural to be present in the xylose liquor.

After the elevated temperature, at least a portion of the resulting xylose liquor may be separated from the glucan solids. The glucan solids may be provided to a saccharification system, in some embodiments. In some implementations, around 70% of the xylose liquor is recovered. In other implementations, about 75% of xylose liquor is recovered.

The xylose liquor, which can still be highly acidic, can be recycled to reduce subsequent acid loading requirements. Makeup acid solution can be added to the xylose liquor and subsequent biomass to help ensure the proper solids to liquids ratio is met. The biomass can again be treated to higher temperatures to yield sugars. The process may be repeated for each subsequent cycle, according to an aspect.

DESCRIPTION OF THE DRAWINGS

In order that the disclosed aspects may be more clearly ascertained, some embodiments will now be described, by way of example, with reference to the accompanying drawings, in which:

FIG. 20A and FIG. 20B list the composition of biomass comprising lignocellulosic plant material from the corn plant according to exemplary and representative embodiments;

FIG. 21A and FIG. 22B list the composition of the liquid component of pre-treated biomass according to exemplary and representative embodiments;

FIG. 22A and FIG. 22B list the composition of the solids component of pre-treated biomass according to exemplary and representative embodiments;

FIG. 23 lists the theoretical acid and water usage for various recycle amounts according to exemplary and representative embodiments;

FIG. 24 lists the experimental conditions for a number of acid recycle examples according to exemplary and representative embodiments; and FIG. 25 lists the results for xylose, glucose, and furfural of the example recycle conditions of FIG. 24 according to exemplary and representative embodiments.

DESCRIPTION OF THE EMBODIMENTS

Various aspects will now be described with reference to several embodiments thereof as illustrated in the accompanying drawings. In the following description, numerous specific details are set forth in order to provide a thorough understanding of embodiments of the various aspects. It will be apparent, however, to one skilled in the art, that embodiments may be practiced without some or all of these specific details. In other instances, well known process steps and/or structures have not been described in detail in order to not unnecessarily obscure the one or more aspects. The features and advantages of embodiments may be better understood with reference to the drawings and discussions that follow.

Aspects disclosed herein relate to systems and methods for acid recycle in a cellulosic acid pretreatment for the generation of ethanol. Such systems and methods can provide cost effective means for decreasing acid and water consumption in a cellulosic ethanol biorefinery while maintaining xylose and glucose yields. For example, provided are systems and methods for pretreatment of biomass in the production of ethanol with reduced acid requirements. Also provided are systems and methods for reducing the need for additional acid, water, and neutralizing agents employed during biomass pretreatment in a cellulosic ethanol biorefinery.

Figure 1A:
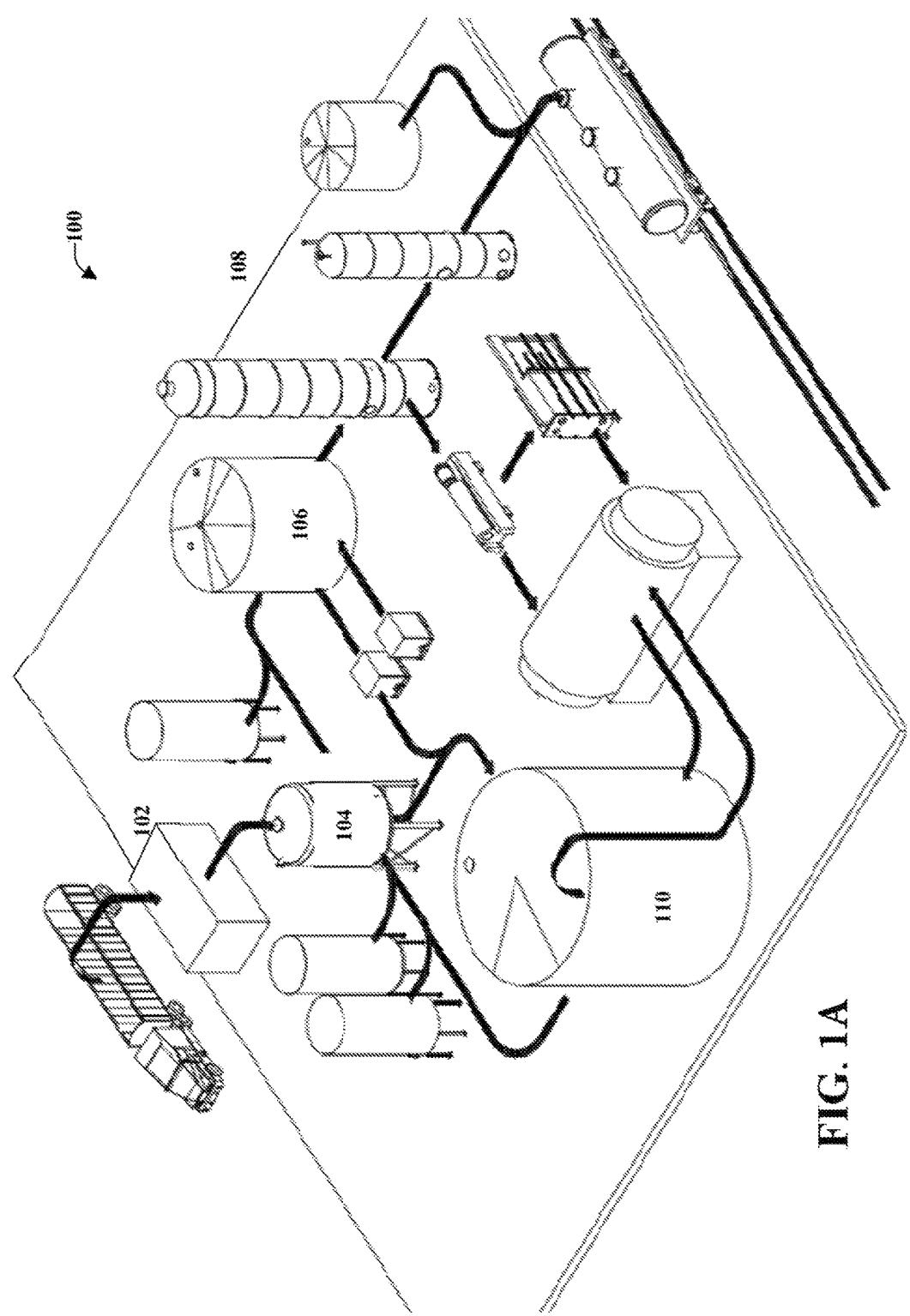
FIG. 1A is a perspective view of a biorefinery comprising an ethanol production facility, in accordance with some embodiments.

Referring to FIG. 1A, an example biorefinery 100 comprising an ethanol production facility configured to produce ethanol from biomass is shown. The example biorefinery 100 comprises an area where biomass is delivered and prepared to be supplied to the ethanol production facility. The cellulosic ethanol production facility comprises apparatus for preparation 102, pre-treatment 104, and treatment of the biomass into treated biomass suitable for fermentation into fermentation product in a fermentation system 106. The cellulosic ethanol production facility comprises a distillation system 108 in which the fermentation product is distilled and dehydrated into ethanol. As shown in FIG. 1A, a waste treatment system 110 (shown as comprising an anaerobic digester and a generator) is included in the biorefinery 100. According to other alternative embodiments, the waste treatment system may comprise other equipment configured to treat, process, and recover components from the cellulosic ethanol production process, such as a solid/waste fuel boiler, anaerobic digester, aerobic digester or other biochemical or chemical reactors.

Figure 1B:
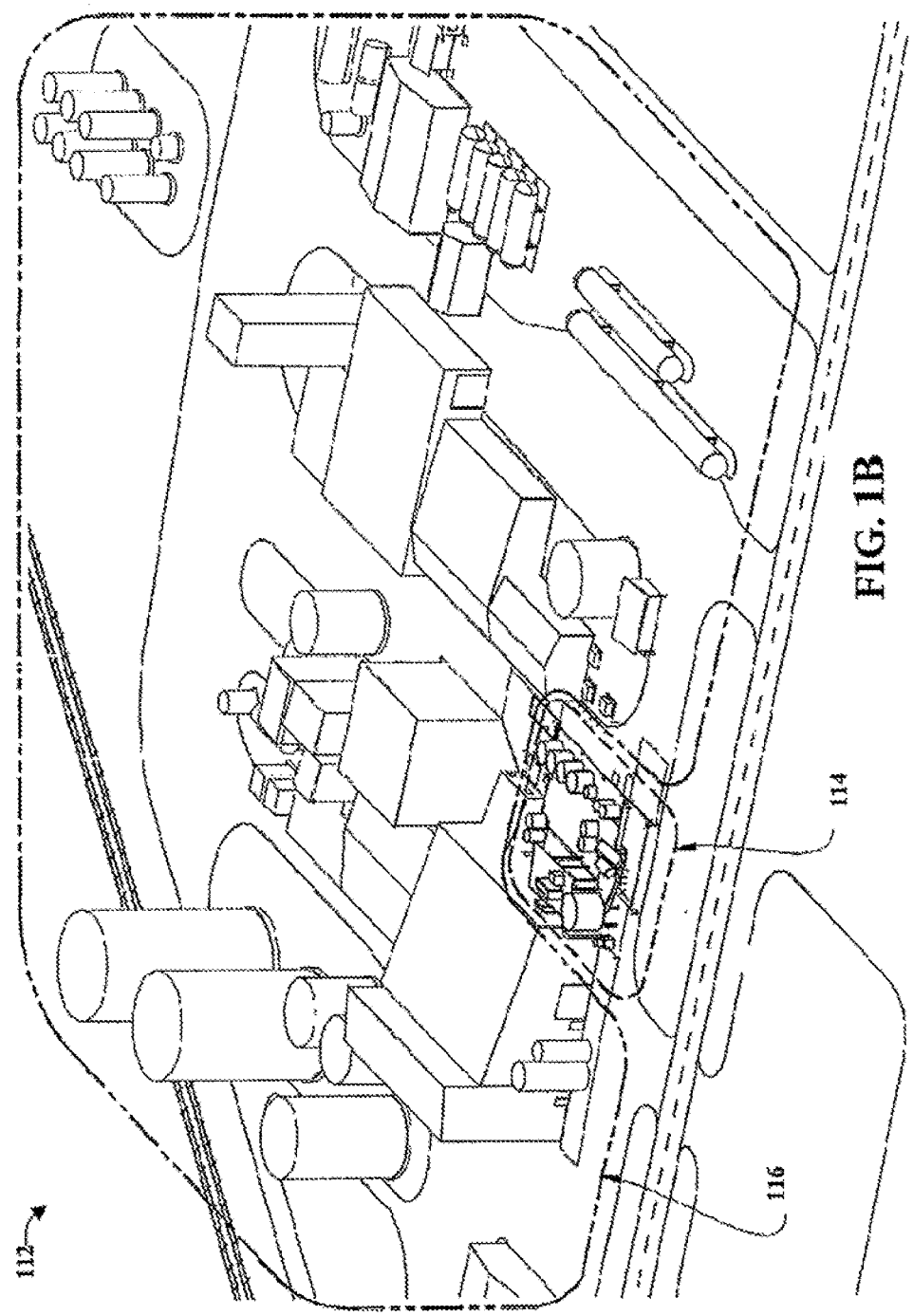
FIG. 1B is another perspective view of a biorefinery comprising an ethanol production facility, in accordance with some embodiments.

As shown in FIG. 1B, according to an exemplary embodiment, a biorefinery 112 may comprise a cellulosic ethanol production facility 114 (which produces ethanol from lignocellulosic material and components of the corn plant) co-located with a corn-based ethanol production facility 116 (which produces ethanol from starch contained in the endosperm component of the corn kernel). As indicated in FIG. 1B, by co-locating the two ethanol production facilities, certain plant systems may be shared, for example, systems for dehydration, storage, denaturing, and transportation of ethanol, energy/fuel-to-energy generation systems, plant management and control systems, and other systems. Corn fiber (a component of the corn kernel), which can be made available when the corn kernel is prepared for milling (e.g. by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g. a cellulosic ethanol production facility) may be co-located with other types of plants and facilities, for example an electric power plant, a waste treatment facility, a lumber mill, a paper plant, or a facility that processes agricultural products.

Figure 2:
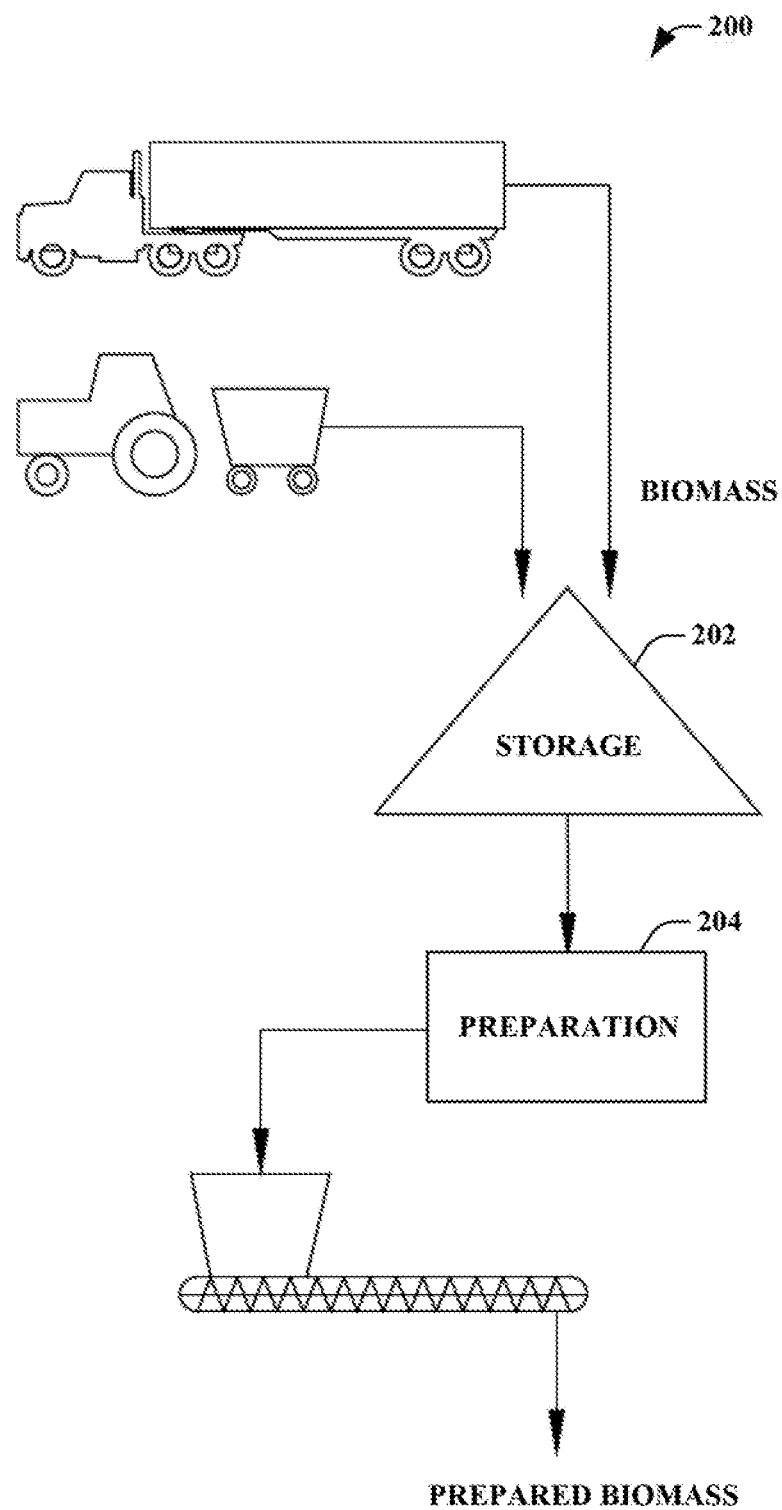
FIG. 2 is a process flow diagram illustrating the preparation of biomass, in accordance with some embodiments.

Referring to FIG. 2, a system 200 for preparation of biomass delivered to the biorefinery is shown. The biomass preparation system may comprise apparatus for receipt/unloading of the biomass, cleaning (e.g. removal of foreign matter), grinding (e.g. milling, reduction or densification), and transport and conveyance for processing at the plant. According to an exemplary embodiment, biomass in the form of corn cobs and stover may be delivered to the biorefinery and stored 202 (e.g. in bales, piles or bins, etc.) and managed for use at the facility. According to an embodiment, the biomass may comprise at least about 20 to about 30 percent corn cobs (by weight) with corn stover and other matter. According to other exemplary embodiments, the preparation system 204 of the biorefinery may be configured to prepare any of a wide variety of types of biomass (e.g.

plant material) for treatment and processing into ethanol and other bioproducts at the plant.

Figure 3A:
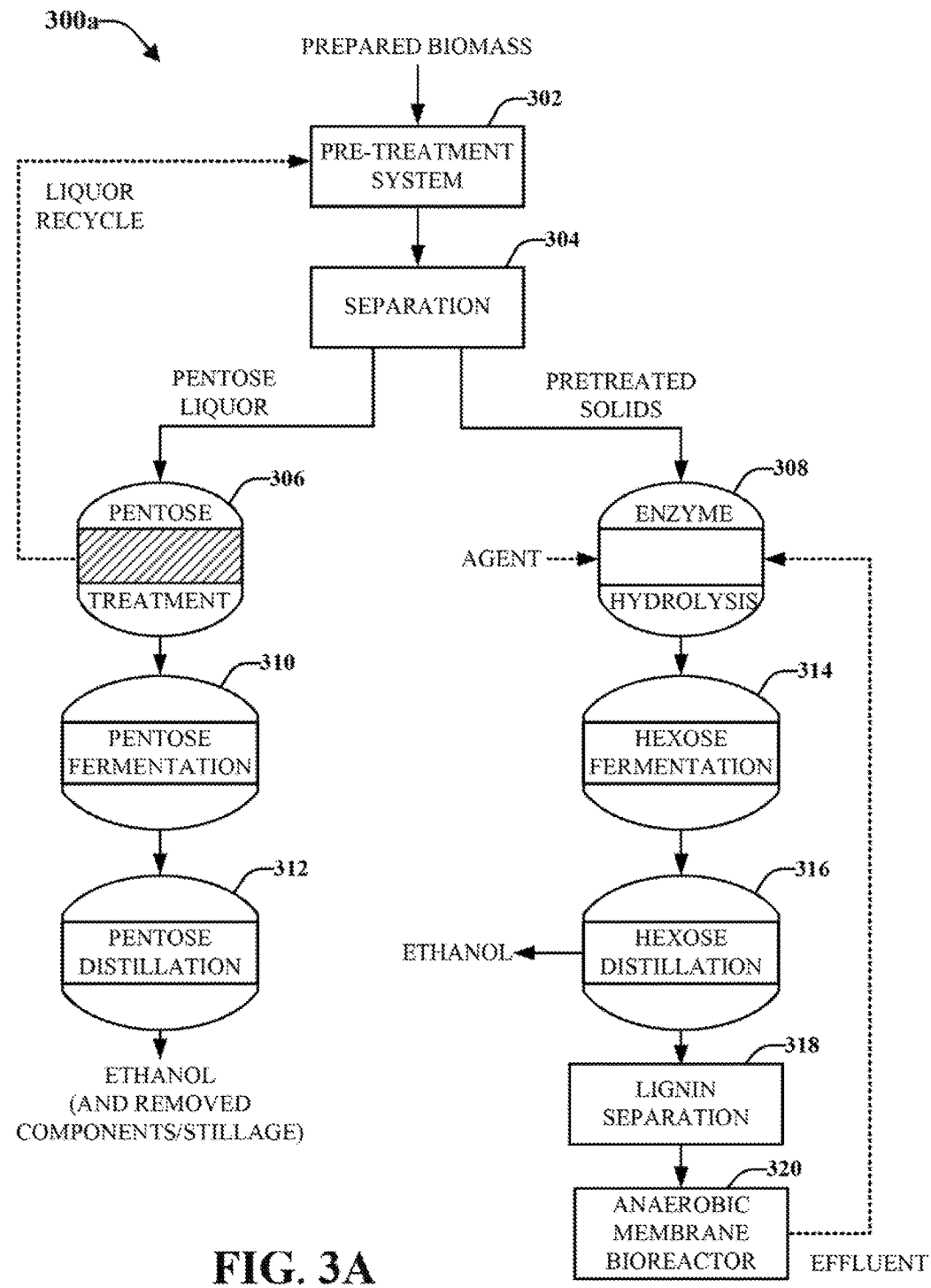
FIGS. 3A and 3B are process flow diagrams illustrating examples of ethanol production processes from biomass to ethanol, in accordance with some embodiments.
Figure 3B:
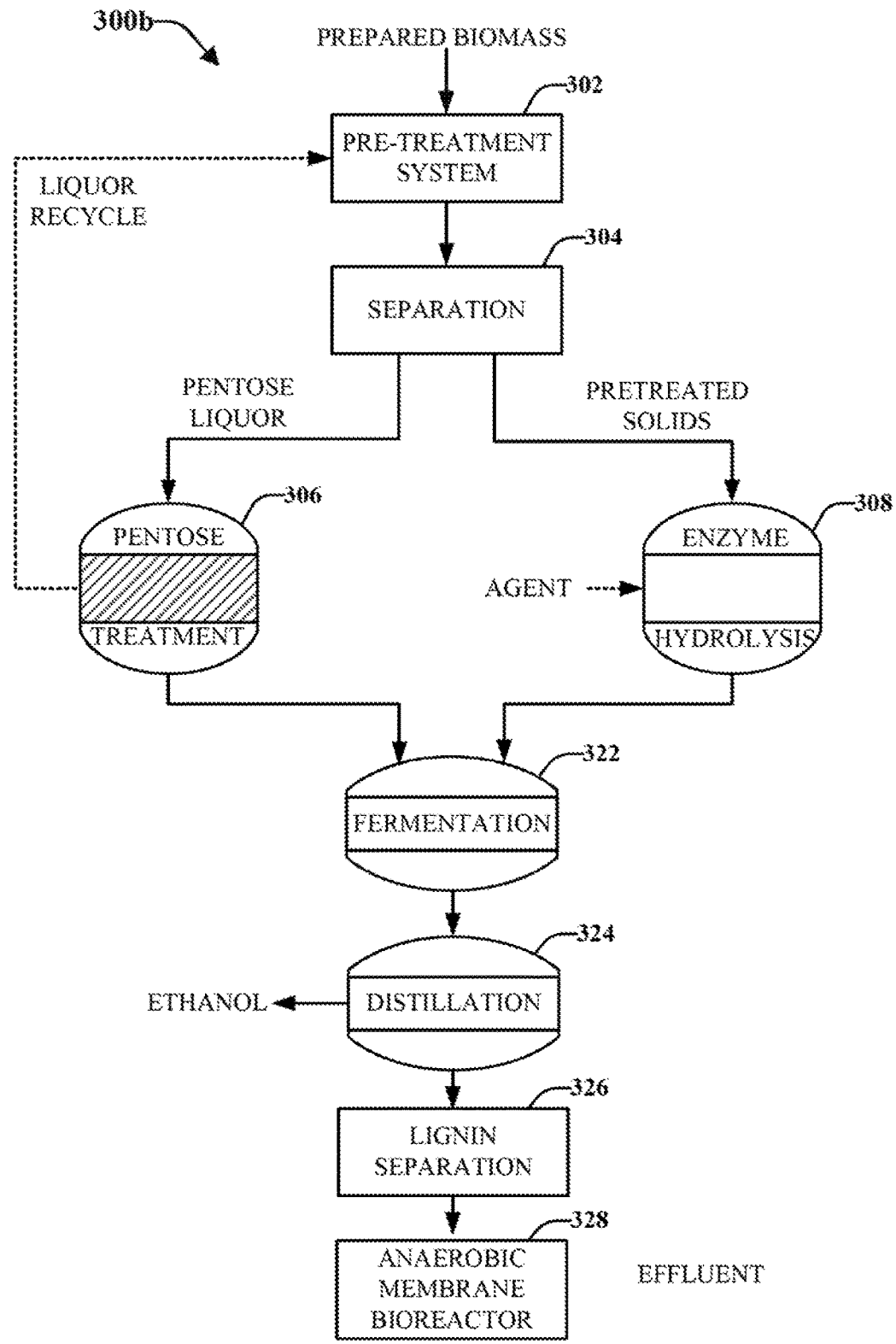

Referring to FIGS. 3A and 3B, alternate embodiments of a schematic diagram of the cellulosic ethanol production facility 300a and 300b are shown. According to some embodiments, biomass comprising plant material from the corn plant is prepared and cleaned at a preparation system. After preparation, the biomass is mixed with water into a slurry and is pre-treated at a pre-treatment system 302. In the pre-treatment system 302, the biomass is broken down (e.g. by hydrolysis) to facilitate separation 304 into a liquid component (e.g. a stream comprising the C5 sugars, known as pentose liquor) and a solids component (e.g. a stream comprising cellulose from which the C6 sugars can be made available). Pretreatment may include the addition of acids in order to lower the pH of the biomass to promote C5 separation. According to some aspects, C5 liquor may also be recycled, as illustrated, from the C5 treatment stage in order to reduce the acid and water levels supplied to the pretreatment system. Specific examples of recycle conditions, volumes, and process conditions will be provided below in greater detail in relation to specific examples. However, other recycle conditions, volumes, and process conditions could also be utilized.

The C5-sugar-containing liquid component (C5 stream or pentose liquor) may be treated in a pentose cleanup treatment system 306. From the pentose cleanup treatment system 306, a recycle stream of xylose liquor may be returned to the pre-treatment system 302 as indicated above.

The C6-sugar-containing pretreated solids component may be treated in a solids treatment system using enzyme hydrolysis 308 to generate sugars. According to an embodiment, hydrolysis (such as enzyme hydrolysis) may be performed to access the C6 sugars in the cellulose; treatment may also be performed in an effort to remove lignin and other non-fermentable components in the C6 stream (or to remove components such as residual acid or acids that may be inhibitory to efficient fermentation). Enzyme hydrolysis efficiency may be increased through the addition of an agent. Such agents may include anaerobic membrane digester effluent, clarified thin stillage, wet cake, whole stillage, other viable protein source, or combinations thereof. Details of the treatment of the C6 solids will be described below.

In accordance with the embodiment of FIG. 3A, the treated pentose liquor may be fermented in a pentose fermentation system 310, and the fermentation product may be supplied to a pentose distillation system 312 for ethanol recovery. In a similar manner, the treated solids, not including substantial amounts of C6 sugars, may be supplied to a hexose fermentation system 314, and the fermentation product may be supplied to a hexose distillation system 316 for ethanol recovery. The stillage from the distillation may be treated at a lignin separation system 318 to generate a liquid component and a solid wet cake. The wet cake may be supplied to an Anaerobic Membrane Bioreactor (AnMBR) 320 for further treatment, in some embodiments.

In the alternate embodiment of FIG. 3B, the resulting treated pentose liquor and treated solids may be combined after treatment (e.g. as a slurry) for co-fermentation in a fermentation system 322. Fermentation product from the fermentation system 322 is supplied to a combined distillation system 324 where the ethanol is recovered. According to one or more embodiments, a suitable fermenting organism (ethanologen) can be used in the fermentation system; the selection of an ethanologen may be based on various considerations, such as the predominant types of sugars present in the slurry. Dehydration and/or denaturing of the ethanol produced from the C5 stream and the C6 stream may be performed either separately or in combination. As with the previously described embodiment, the stillage from the distillation may be treated at a lignin separation system 326 to generate a liquid component and a solid wet cake. The wet cake may then be supplied to an Anaerobic Membrane Bioreactor (AnMBR) 328 for further treatment, in some embodiments.

During treatment of the C5 and/or C6 stream, components may be processed to recover byproducts, such as organic acids and lignin. The removed components during treatment and production of ethanol from the biomass from either or both the C5 stream and the C6 stream (or at distillation) can be treated or processed into bioproducts or into fuel (such as lignin for a solid fuel boiler or methane produced by treatment of residual/removed matter such as acids and lignin in an anaerobic digester) or recovered for use or reuse.

According to an embodiment, the biomass comprises plant material from the corn plant, such as corn cobs, corn plant husks and corn plant leaves and corn stalks (e.g. at least upper half or three-quarters portion of the stalk); the composition of the plant material (e.g. cellulose, hemicellulose and lignin) can be approximately as indicated in FIG. 20A and FIG. 20B (e.g. after at least initial preparation of the biomass, including removal of any foreign matter). According to an embodiment, the plant material comprises corn cobs, husks/leaves and stalks; for example, the plant material may comprise (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any of a wide variety of other combinations of cobs, husks/leaves and stalks from the corn plant. See FIG. 20A. According to an alternative embodiment, the lignocellulosic plant material may comprise fiber from the corn kernel (e.g. in some combination with other plant material). FIG. 20B provides typical and expected ranges believed to be representative of the composition of biomass comprising lignocellulosic material from the corn plant. According to exemplary embodiments, the lignocellulosic plant material of the biomass (from the corn plant) can comprise (by weight) cellulose at about 30 to about 55 percent, hemicellulose at about 20 to about 50 percent, and lignin at about 10 to about 25 percent; according to a particular embodiment, the lignocellulosic plant material of the biomass (e.g. cobs, husks/leaves and stalk portions from the corn plant) can comprise (by weight) cellulose at about 35 to about 45 percent, hemicellulose at about 24 to about 42 percent, and lignin at about 12 to about 20 percent. According to a particular embodiment, pre-treatment of the biomass can yield a liquid component that comprises (by weight) xylose at no less than approximately 1.0 percent and a solids component that comprises (by weight) cellulose (from which glucose can be made available) at no less than around 45 percent.

Figure 4:
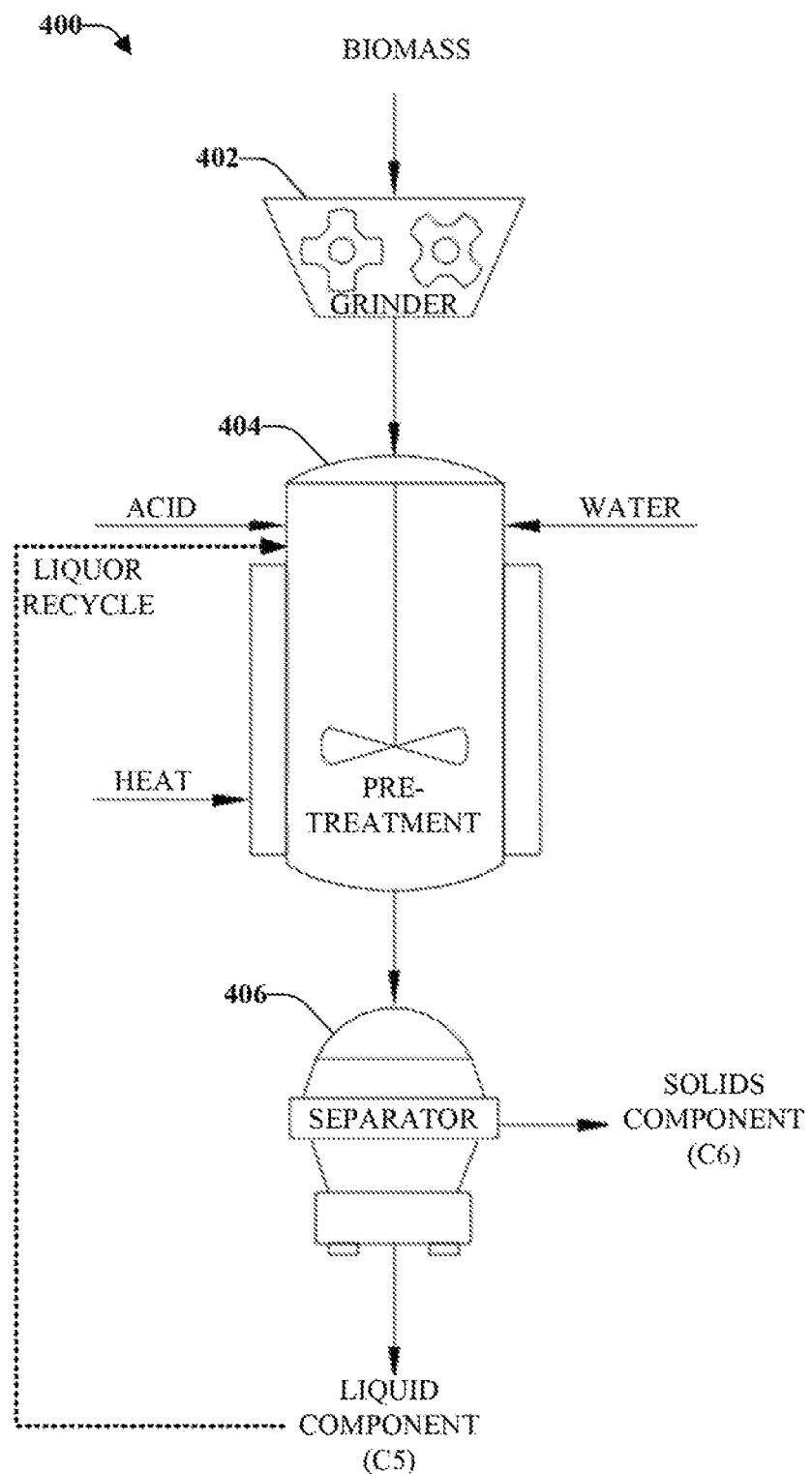
FIG. 4 is an apparatus used for the preparation, pre-treatment, and separation of lignocellulosic biomass, in accordance with some embodiments.

FIG. 4 shows an apparatus 400 used for preparation, pre-treatment, and separation of lignocellulosic biomass according to an exemplary embodiment. As shown, biomass is prepared in a grinder 402 (e.g. a grinder or other suitable apparatus or mill). Pre-treatment of the prepared biomass is performed in a reaction vessel 404 (or set of reaction vessels) supplied with prepared biomass, acid, and/or water in a predetermined concentration (or pH) and other operating conditions. The pre-treated biomass can be separated in a centrifuge 406 into a liquid component (C5 stream comprising primarily liquids with some solids) and a solids component (C6 stream comprising liquids and solids such as lignin and cellulose from which glucose can be made available by further treatment).

According to an embodiment, in the pre-treatment system an acid can be applied to the prepared biomass to facilitate the breakdown of the biomass for separation into the liquid (pentose liquor) component (C5 stream from which fermentable C5 sugars can be recovered) and the solids component (C6 stream from which fermentable C6 sugars can be accessed). According to some embodiments, the acid can be applied to the biomass in a reaction vessel under determined operating conditions (e.g. acid concentration, pH, temperature, time, pressure, solids loading, flow rate, supply of process water or steam, etc.) and the biomass can be agitated/mixed in the reaction vessel to facilitate the breakdown of the biomass. According to exemplary embodiments, an acid such as sulfuric acid, hydrochloric acid, nitric acid, phosphoric acid, acetic acid, etc. (or a formulation/mixture of acids) can be applied to the biomass in combination with a xylose liquor recycle stream. The xylose liquor recycle stream includes enzymes, acid, and water that may reduce the requirements for additional acid and water to be added at the pretreatment system. Maximization of sugar liberation and minimization of inhibitor generation may be achieved by carefully controlling xylose recycle volumes and process conditions. FIG. 23 provides theoretical acid and water utilized for pretreatments dependent upon volume of xylose liquor recycled during the pretreatment step. Additionally, economic data relating to the cost for the new acid is provided. Acid/Water usage was calculated for 10 pretreatment cycles using varying amounts of recycled liquor. The calculations were based on 1000 kg of cob at a 14.3% solids loading, using 1% $H_2SO_4$. Recycling a larger amount of xylose liquor into the next pretreatment results in a larger percentage reduction in the amount of acid and water utilized in subsequent pretreatments. It was also found that by recycling liquor there is an increase in the xylose concentration of the xylose liquor proportional to the amount of liquor being recycled. There is a maximum amount of liquor that can be recycled based on liquor availability due to liquid solid separation efficiency and the amount of liquor taken from the process as a liquor stream. As illustrated, with larger volumes of xylose liquor recycle, water usage and acid addition decreases significantly. Up to around a 70% reduction in water and acid can be achieved, in some embodiments.

Figure 5:
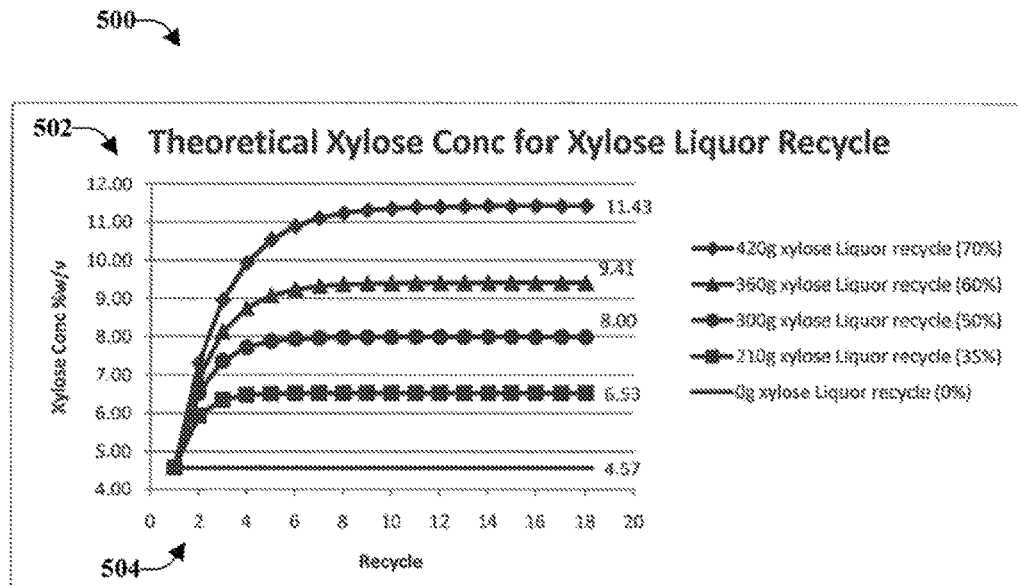
FIG. 5 is an example graph of the theoretical xylose concentration for xylose liquor recycles, in accordance with some embodiments.

FIG. 5 illustrates an example graph 500 of the theoretical concentration 502 for xylose in the xylose liquor stream for various recycle volumes over a number of cycles 504, according to an embodiment. The theoretical xylose concentration was calculated for a xylose liquor recycle based on a 14.3% solids pretreatment with 100% xylose yield using cob with 32 g xylose per 100 g cob (e.g. 320 kg xylose per metric ton). The xylose concentration 502 was calculated by assuming 32 g of xylose in 700 g of solution from pretreatment, leading to a concentration of 4.57% for the first pretreatment. Then, an amount of liquor would be recycled into the next pretreatment carrying with it a certain amount of xylose that would be in addition to the amount of xylose produced during pretreatment of 100 g cob (32 g xylose). With subsequent cycles, the xylose concentrations increased until the xylose concentrations leveled out at a steady state value. The larger the recycle volume, the more xylose that is returned to the pretreatment, thereby further increasing the outbound xylose concentration until saturation. For example, according to the theoretical values in FIG. 5, at a 70% xylose liquor recycle final xylose concentration after 20 cycles is estimated to reach about 11.43% w/v.

Figure 6:
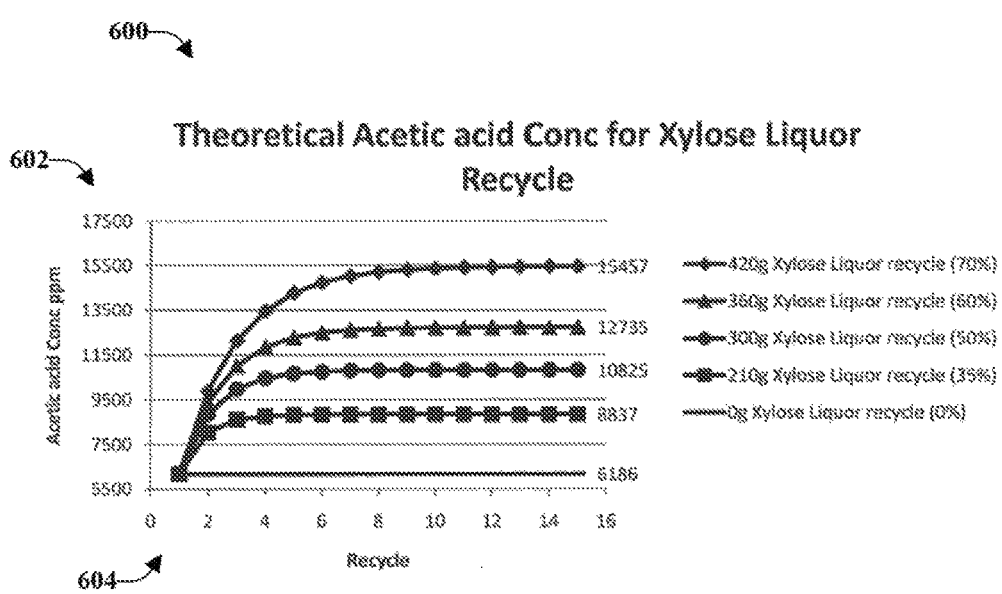
FIG. 6 is an example graph of the theoretical acetic acid concentration for xylose liquor recycles, in accordance with some embodiments.

In a similar manner, FIG. 6 illustrates an example graph 600 of the theoretical concentration for acetic acid 602 (a fermentation inhibitor at some concentrations) in the xylose liquor stream for various recycle volumes over a number of cycles 604, according to an aspect. Similar condition assumptions to those used in FIG. 5 were used to model acetic acid concentrations. The first cycle, on average, produces an acetic acid concentration of about 6186 ppm. With subsequent cycles, the acetic acid concentrations increased until the acetic acid concentrations leveled out at a steady state value. The larger the recycle volume, the more acetic acid that is returned to the pretreatment, thereby further increasing the outbound acetic acid concentration until saturation. For example, according to the theoretical values in FIG. 6, at a 70% xylose liquor recycle final acetic acid concentration after 16 cycles is estimated to reach about 15457 ppm.

According to a particular embodiment, sulfuric acid can be applied to the biomass in pre-treatment in addition to the xylose liquor recycle stream. According to a particular embodiment, the prepared biomass may be pretreated with approximately 0.8 to approximately 1.5 percent acid (such as sulfuric acid) and about 12 to about 25 percent biomass solids at a temperature of approximately 100 to about 180 degrees Celsius for approximately 5 to around 180 minutes. In alternate embodiments, xylose liquor is supplied to the biomass at a set volume. The pH of the biomass is then adjusted to about 1.5 using concentrated acid, such as sulfuric acid. The use of a xylose recycle stream reduces the total new mineral acid that is needed to bring the pH to acceptable levels for pretreatment. The pre-treatment may also comprise a steam explosion step, where biomass is heated to and held at (e.g. hold time) approximately 150 to approximately 165 degrees Celsius under pressure (e.g. 100 psi) at a pH of about 1.4 to about 1.6 for around 1 to around 15 minutes, and the pressure is released to further aid in the breakdown of cellulose. After pretreatment the pre-treated biomass is separated into a solids component (C6) and a liquid pentose liquor component (C5), as shown in FIG. 4.

The liquid pentose liquor component (C5 stream) comprises water, dissolved sugars (such as xylose, arabinose, and glucose) to be made available for fermentation into ethanol, acids, and other soluble components recovered from the hemicellulose. (FIG. 21B provides typical and expected ranges believed to be representative of the composition of biomass comprising lignocellulosic material from the corn plant.) According to an exemplary embodiment, the liquid component may comprise approximately 5 to approximately 7 percent solids (e.g. suspended/residual solids such as partially hydrolysed hemicellulose, cellulose, and lignin). According to a particular embodiment, the liquid component comprises at least about 2 to about 4 percent xylose (by weight); according to other exemplary embodiments, the liquid component comprises no less than around 1 to around 2 percent xylose (by weight). FIG. 21A and FIG. 21B list the composition of the liquid component of pre-treated biomass (from prepared biomass as indicated in FIG. 20A and FIG. 20B) according to exemplary and representative embodiments. A portion of the C5 xylose liquid liquor stream may be recycled to the pretreatment as described above. In some embodiments, all (or substantially all) of the xylose liquor may be recycled. In the embodiments where all (or substantially all) of the xylose liquor is not recycled the remaining xylose liquor that is not recycled may be treated with an alkali (such as sodium hydroxide, lime, or ammonium hydroxide) prior to being introduced to fermentation. Additional inhibitor removal treatments may be performed on the xylose liquor, in some embodiments.

The solids component (C6 stream) comprises water, acids, and solids such as cellulose from which sugar, such as glucose, can be made available for fermentation into ethanol and lignin. (FIG. 22B provides typical and expected ranges believed to be representative of the composition of biomass comprising lignocellulosic material from the corn plant.) According to an exemplary embodiment, the solids component may comprise approximately 10 to approximately 40 percent solids (by weight) (after separation); according to a particular embodiment, the solids component can comprise approximately 20 to approximately 30 percent solids (by weight). According to another embodiment, the solids in the solids component comprise no less than about 30 percent cellulose and the solids component may also comprise other dissolved sugars (e.g. glucose and xylose). FIG. 22A and FIG. 22B list the composition of the solids component of pre-treated biomass (from prepared biomass as indicated in FIG. 20A and FIG. 20B) according to exemplary and representative embodiments.

After the separation of the C5 liquid component from the C6 solids, the solids may be treated further in an enzymatic hydrolysis system. According to an embodiment, after pre-treatment, the solids component (C6) is supplied to a vessel for enzymatic hydrolysis (or saccharification) along with enzymes, agents, and water. The enzymes can facilitate the breakdown of pre-treated cellulose into sugar (e.g. glucose) to generate an enzymatic hydrolysis product. This sugar rich enzymatic hydrolysis product may then be fermented into ethanol, or used for any other downstream process.

In some embodiments, the C6 solids may be subjected to a sequential hydrolysis and fermentation (SHF) process, wherein the solids are subjected to an enzyme hydrolysis (with a glucan conversion of at least 80%) followed by a fermentation. While using a two-step process, with the SHF approach enzyme hydrolysis may be performed at optimal pH (or as near an optimal pH as possible) and temperature for conversion of cellulose to sugars. For SHF, the solids are treated at about 50° C., around 5.5 pH, and about 15% total solids slurry with cellulase.

Alternatively, the C6 solids may be subjected to a simultaneous (or almost simultaneous) saccharification and fermentation (SSF) process wherein the enzyme hydrolysis and fermentation is performed at about the same time. Simultaneous (or near simultaneous) saccharification and fermentation can be performed at temperatures suitable for ethanol production by the yeast (e.g., about 37° C.) which can be less than optimal for the cellulase enzyme, according to an aspect.

According to an exemplary embodiment, an enzyme formulation comprising an enzyme capable of hydrolysing cellulose is supplied to the solids component (C6) to facilitate the enzyme hydrolysis, e.g. the saccharification by enzyme action of the polymeric cellulose (e.g. polymeric glucan) into accessible monomeric sugars (e.g. monomeric glucose). An example of such cellulase enzyme is Cellic CTec (e.g. NS22074) from Novozymes North America, Inc. of Franklinton, N.C. The amount or loading (dose) of enzyme formulation may be varied as an operating condition. According to an exemplary embodiment, approximately 2 to approximately 12 milligrams of enzyme protein per gram of cellulose may be added. According to a particular embodiment, approximately 3 to approximately 9 milligrams of enzyme protein per gram of cellulose may be added.

According to an exemplary embodiment, the temperature during the treatment of the solids component (C6) may be approximately 30 to approximately 60 degrees Celsius. According to an embodiment, the temperature during the treatment of the solids component (C6) may be approximately 45 to approximately 55 degrees Celsius, and according to a particular embodiment, the temperature during the treatment of the solids component (C6) may be approximately 49 to around 51 degrees Celsius.

According to an exemplary embodiment, the treatment time of the solids component (C6) may be approximately 48 to about 144 hours. According to an embodiment, the treatment time of the solids component (C6) may be approximately 60 to approximately 120 hours, and according to a particular embodiment, the treatment time of the solids component (C6) may be around 72 to about 96 hours.

According to an exemplary embodiment, the solids content of the solids component (C6) supplied to the treatment system may be approximately 5 to approximately 25 percent by weight. According to an embodiment, the solids content of the solids component (C6) may be approximately 10 to approximately 20 percent by weight, and according to a particular embodiment, the solids content of the solids component (C6) may be approximately 12 to approximately 17 percent by weight.

According to an exemplary embodiment, the pH during the treatment of the solids component (C6) may be approximately 4.8 to about 6.2. According to an embodiment, the pH during the treatment of the solids component (C6) may be approximately 5.2 to around 5.8, and according to a particular embodiment, the pH during the treatment of the solids component (C6) may be approximately 5.4 to approximately 5.6.

A glucose yield that may be achieved during enzyme hydrolysis of biomass (e.g. corn cobs, husks, leaves and/or stalks) using available cellulase enzymes without the addition of thin stillage, clarified thin stillage, or anaerobic membrane bioreactor effluent may be in the range of around 35 to around 40 percent of theoretical (e.g. calculated) glucose yield for simultaneous (or almost simultaneous) saccharification and fermentation (SSF) and between about 55 to about 70 percent of theoretical glucose yield for sequential hydrolysis and fermentation (SHF). Exact glucose yields may vary dependent upon pretreatment procedures. For example, inclusion of steam explosion pretreatment, as described above, may increase glucose conversion yields for SHF processed biomass.

As discussed herein, an aspect relates to a method for pretreating lignocellulosic biomass. The method can include applying an acid solution to a first portion of biomass and maintaining an elevated temperature of the first portion of biomass such that a xylose yield of greater than about 80% of theoretical is achieved. A liquid xylose liquor and a glucan solid are produced from the first portion of biomass while maintaining the elevated temperature. The method can also include separating at least a portion of the liquid xylose liquor from the glucan solid, applying the portion of the liquid xylose liquor to a subsequent portion of the biomass, and applying a makeup acid solution to the subsequent portion of the biomass. Further, the method can include maintaining an elevated temperature of the subsequent portion of the biomass such that xylose yield of greater than about 80% of theoretical is achieved. A liquid xylose liquor and a glucan solid are produced from the subsequent portion of the biomass while maintaining the elevated temperature. The method can repeat starting with separating the portion of the liquid xylose liquor to a subsequent portion of the biomass. In some implementations, the method can include releasing sugar glucose.

In an example, maintaining the elevated temperature can include maintaining the temperature at about 120° C. and 150° C. In another example, maintaining the elevated temperature can include maintaining the elevated temperature for at least about 10 minutes. In a further example, maintaining the elevated temperature can include maintaining the elevated temperature for less than about 120 minutes.

In some implementations, applying the acid solution can include applying an acid solution that is between about 1% to 1.6% sulfuric acid. In some implementations, the elevated temperature of the first portion of biomass and the elevated temperature of the subsequent portion of the biomass can be maintained until greater than about 90% of theoretical xylose yield is achieved. In other implementations, the elevated temperature of the first portion of biomass and the elevated temperature of the subsequent portion of the biomass can be maintained until greater than about 45% of theoretical glucose yield is achieved. In some implementations, the elevated temperature of the first portion of biomass and the elevated temperature of the subsequent portion of the biomass can be maintained until greater than about 50% of theoretical glucose yield is achieved.

In an aspect, the liquid xylose liquor comprises less than about 4000 ppm furfural. In some aspects, the liquid xylose liquor comprises less than about 3000 ppm furfural. According to some aspects, the portion of the liquid xylose liquor is about 70% of the total xylose liquor. According to other aspects, the portion of the liquid xylose liquor is about 75% of the total xylose liquor.

Another aspect relates to a method for pretreating lignocellulosic biomass to be supplied to a fermentation system for production of a fermentation product. The method can include applying a xylose liquor to biomass, applying a makeup acid solution to the biomass, and maintaining an elevated temperature of the biomass such that a xylose yield of greater than about 80% of theoretical is achieved. Xylose liquor and a glucan solid can be produced from the biomass while maintaining the elevated temperature. The method can also include separating at least some portion of the xylose liquor from the glucan solid. The method can repeat with applying an acid solution to the biomass.

EXAMPLES

A series of limited examples were conducted according to an exemplary embodiment of the system in an effort to evaluate the effect of varying recycle volumes and process conditions. Experiments and tests were conducted to evaluate xylose concentrations, glucose yields, acetic acid concentrations, and inhibitor levels (such as furfural) as a function of recycle volume, cycle number, and process conditions. The following examples are intended to provide clarity to some embodiments of systems and means of operation and are not intended to limit the scope of the various aspects disclosed herein.

FIG. 24 provides an overview of the example experimental conditions, including pretreatment temperature, cycle numbers, sulfuric acid concentration, and timing. For all examples, sugar, furfural/5-hydroxy-methylfurfural (HMF), and acetic acid levels were measured utilizing known HPLC (High-Performance Liquid Chromatography) analytical techniques. Glucose concentrations were measured after a saccharification step. Further, pretreatment makeup was adjusted for moisture variability of the ground biomass samples. For each example condition, all (or substantially all) pretreatment liquor was used to recycle to the next cycle (excluding a small test volume for analytics).

For all examples, cob material was hammer milled and stored in a Quonset but style building to maintain a dry environment with minimal or no exposure to the sun and inclement weather. Sulfuric acid was obtained from Fisher Scientific (of Waltham, Mass.) in reagent form for the Babcock Milk Test SA174-4 91.6% acid.

The ground cob was used to make a 14.3% solids solution with acid solution containing the prescribed concentration of acid for the pretreatment conditions as presented in FIG. 24. The 1 L Parr reactor vessel was loaded with 100 g of ground cob on a dry weight basis; water and sulfuric acid were combined to achieve the desired acid concentration in the liquid fraction while accounting for water brought in with the biomass and then added to the raw biomass. The acid solution and cobs were stirred with a spatula to wet the entire sample. The vessel was then connected to the Parr reactor head and stirred at 450 rpm. Heat was applied by supplying high pressure steam (250 to 300 psi) into the vessel jacket. The temperature was monitored using a thermocouple in the external thermowell. The heat was adjusted accordingly by adding either steam or cold water to the vessel jacket. The reaction timer started as soon as the vessel contents reached the desired temperatures. After the vessel had been held at temperature for the appropriate amount of time, the vessel was cooled using water through the vessel jacket.

After the reaction was complete, the Parr reactor vessel was removed and the pretreatment slurry was transferred into a tared 1000 ml polypropylene centrifuge tube. The slurry was then separated via centrifuge at 4500 rpm for 15 minutes. The moisture level of the solids was determined using an oven moisture procedure, and then submitted for enzymatic saccharification. A 30 g sample of the xylose liquor was taken for sugar (xylose, glucose, and arabinose), HMF, Furfural, acetic acid, and total solids (dissolved and suspended) analysis. The remaining mass of liquor was used as recycle liquid for the next pretreatment.

Subsequently, the solids were diluted to 10% with water. Hydrolysis was performed in 125 ml Erlenmeyer flasks with 70 ml of slurry. The slurries in each flask were pH adjusted to 5.5 using 45% w/w aqueous potassium hydroxide or 10% v/v aqueous sulfuric acid. Enzyme loadings were 9 mg enzyme protein per g glucan (the glucan content of the solids portion was assumed as 35%). The flasks were incubated in a water bath shaker at 50° C. (stirred at 150 rpm) for 72/96 hours.

The recycle process was performed by loading the Parr reactor vessel with 100 g ground cob on a dry weight basis, the recycle liquid from the previous pretreatment was added, the reaction mass was adjusted to 700 g using a dilute acid solution with appropriate acid concentration from FIG. 24. The process for pretreatment was then carried out identically (or nearly identically) for each recycle step. This recycle process was repeated for the number of times designated in the experimental design.

In the example experiment, xylose concentration, glucose concentration, and acetic acid concentration for each of the conditions illustrated in TABLE 5 were analyzed. Xylose liquor was collected and filtered through a 0.2 μm syringe into HPLC vials. The vials were then loaded onto a carousel, which fits into an auto sampler (either 717 plus or 2659 separations module from Waters of Milford, Mass.). An aliquot (5 μl) of the sample was injected by the auto-injector onto a reverse phase column (HPX-87H from Bio-Rad Laboratories of Hercules, Calif.) maintained at 50° C. Sulfuric acid at 0.005M was used as the mobile phase (eluent). The HPLC system was equipped with a refractive index detector (either the 2410 or 2414 model from Waters). The components (sugars, organic acids, and ethanol) were identified and quantified using the Empower software (Waters).

Furfural and HMF concentration for each of the conditions illustrated at FIG. 24 were analyzed. Samples were prepared by diluting the xylose liquor tenfold with water and filtering through a 0.2 µm nylon syringe filter into HPLC vials. A 10 µl aliquot was injected by the HPLC autosampler (Dionex Ultimate 3000) onto a reversed phase HPLC C18 column at 40° C. The samples were eluted with a mobile phase consisting of a solution of 90:5:5 water:acetonitrile: methanol at a flow rate of 1 ml/min. Furfural and HMF were detected by UV at 280 nm wavelength. Late eluting compounds were washed off the column by a column wash mobile phase consisting of 50:10:40 water:acetonitirle: methanol at 1 ml/ml for 5 min.

Figure 7:
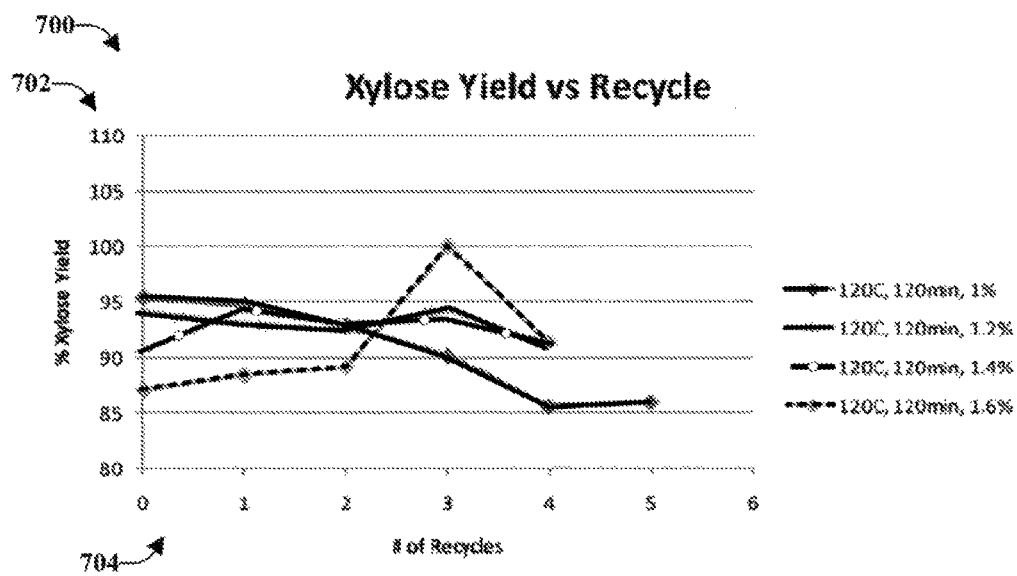
FIGS. 7-10 are example graphs of the xylose concentration in pretreated biomass as a function of recycle numbers for various process conditions, in accordance with some embodiments.
Figure 8:
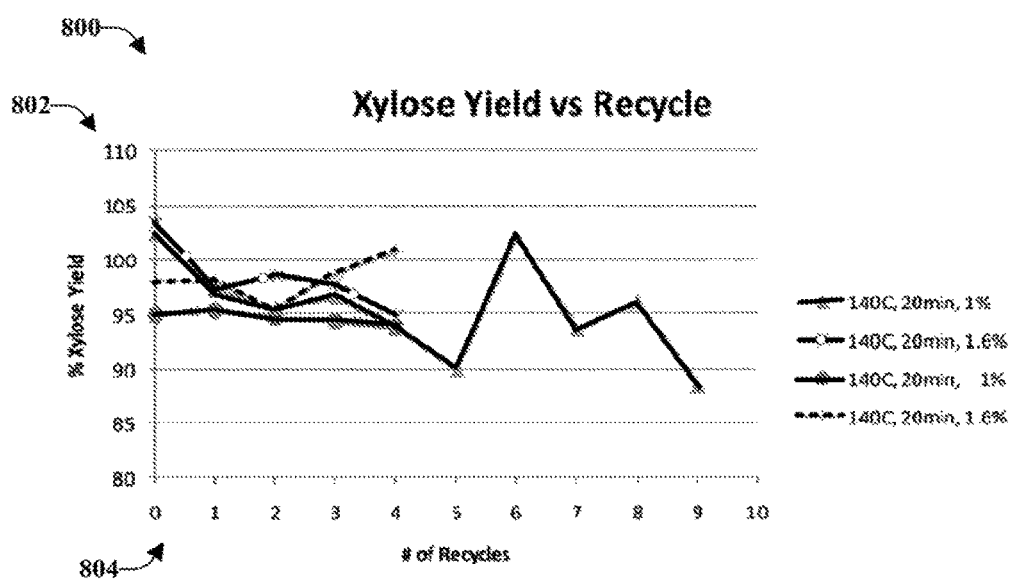
Figure 9:
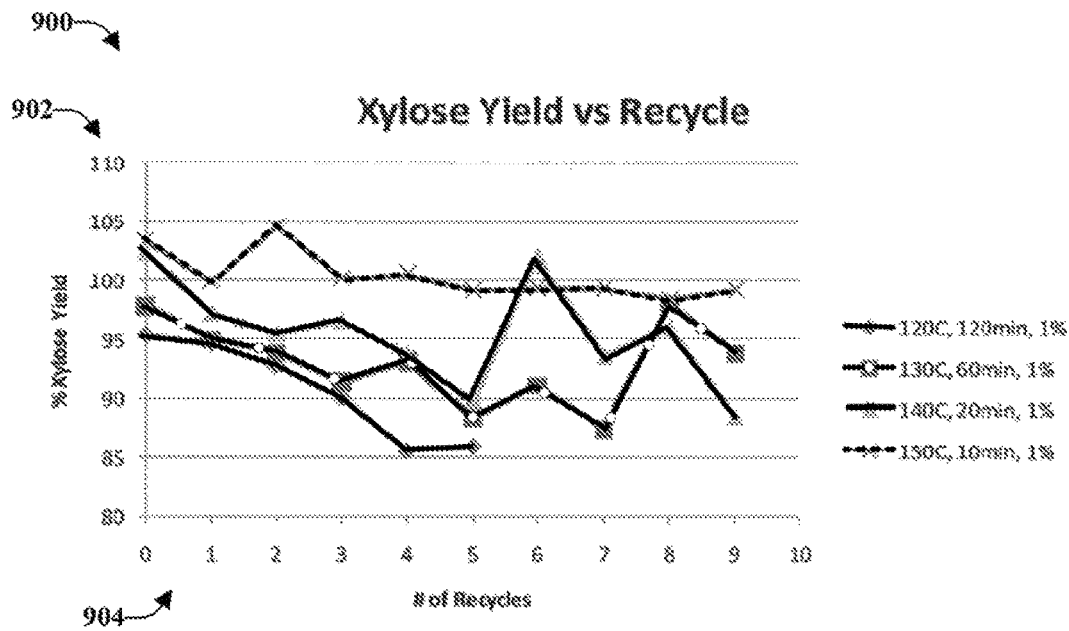
Figure 10:
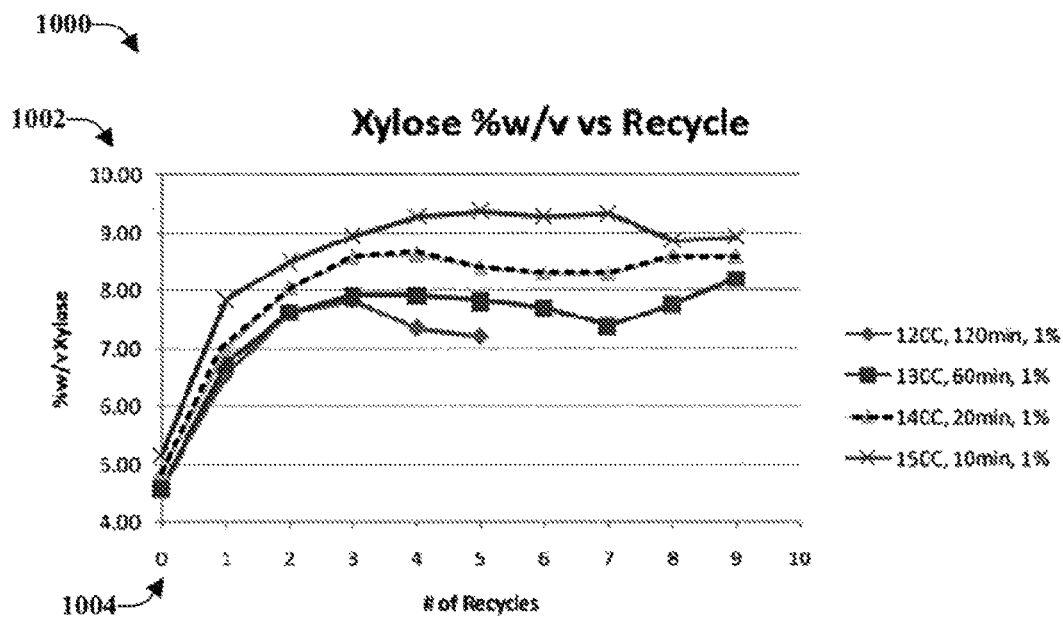

Results for the analysis of xylose as a function of number of recycles are illustrated in the graphs of FIGS. 7-10. In particular, FIG. 7 illustrates an example graph 700 of the percent xylose yields 702 for the samples treated at 120° C. for 120 minutes at varying acid solutions for different cycles 704 (as detailed in FIG. 24). FIG. 8 illustrates an example graph 800 of the percent xylose yields 802 for the samples treated at 140° C. for 20 minutes at varying acid solutions for a number of different cycles 804 (as detailed in FIG. 24). FIG. 9 illustrates an example graph 900 of the percent xylose yields 902 for the samples treated with a 1% acid solution at varying times and temperatures over a number of different cycles 904 (as detailed in FIG. 24). FIG. 10 illustrates an example graph 1000 of the percent xylose (w/v) 1002 in the pretreatment liquor as a function of recycle numbers 1004. As illustrated, xylose concentrations increase as recycle numbers increase until a steady state concentration is reached. In this example embodiment, the greatest overall xylose yield was achieved using a 10 minute pretreatment with 1% acid solution and 150° C. temperature.

Figure 11:
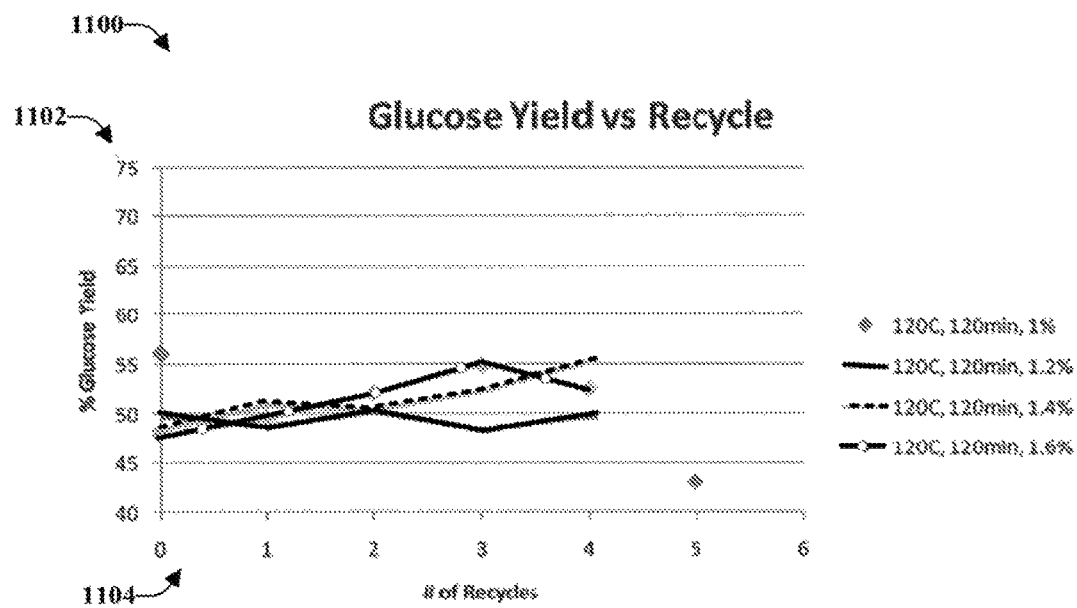
FIGS. 11-13 are example graphs of the glucose concentration in pretreated biomass as a function of recycle numbers for various process conditions, in accordance with some embodiments.
Figure 12:
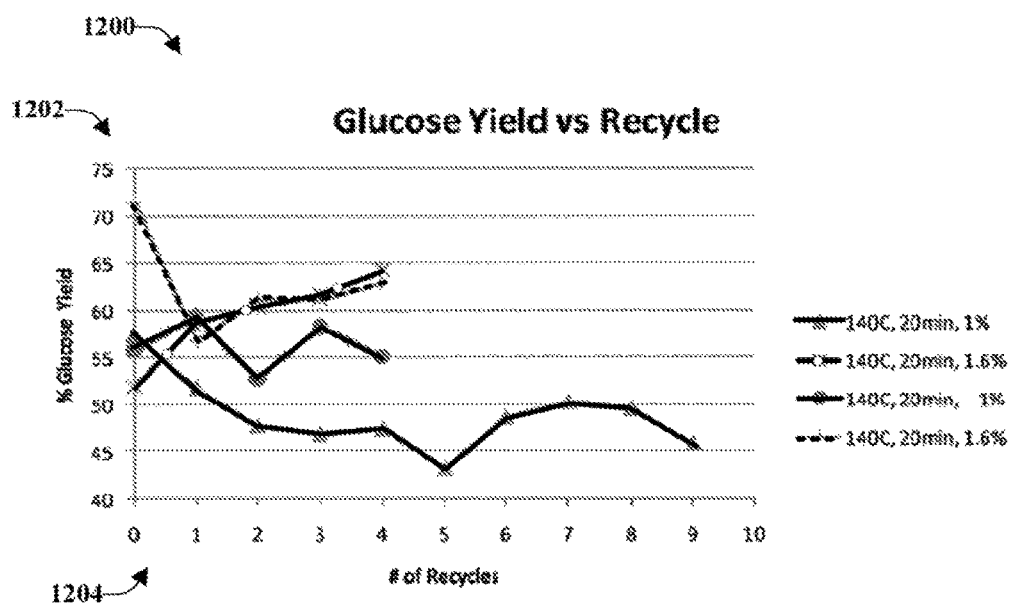
Figure 13:
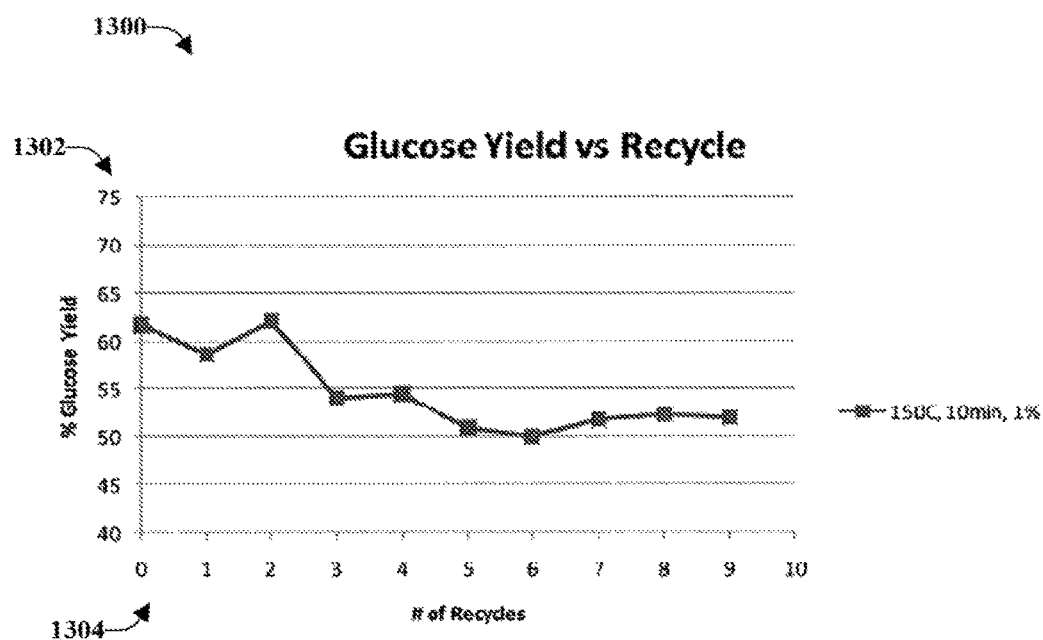

Results for the analysis of glucose as a function of number of recycles are illustrated in the graphs of FIGS. 11-13. In particular, FIG. 11 illustrates an example graph 1100 of percent glucose yields 1102 for the samples treated at 120° C. for 120 minutes at varying acid solutions as a function of recycle numbers 1104 (as detailed in FIG. 24). FIG. 12 illustrates an example graph 1200 of percent glucose yields 1202 for the samples treated at 140° C. for 20 minutes at varying acid solutions as a function of recycle numbers 1204 (as detailed in FIG. 24). FIG. 13 illustrates an example graph 1300 of percent glucose yields 1302 for the samples treated at 150° C. for 10 minutes with a 1% acid solution as function of recycle numbers 1304 (as detailed in FIG. 24). As illustrated, glucose yields increase with each recycle at the 120° C. conditions. However, at 140° C. conditions and 150° C. condition, glucose yields are variable over the successive recycles.

Figure 14:
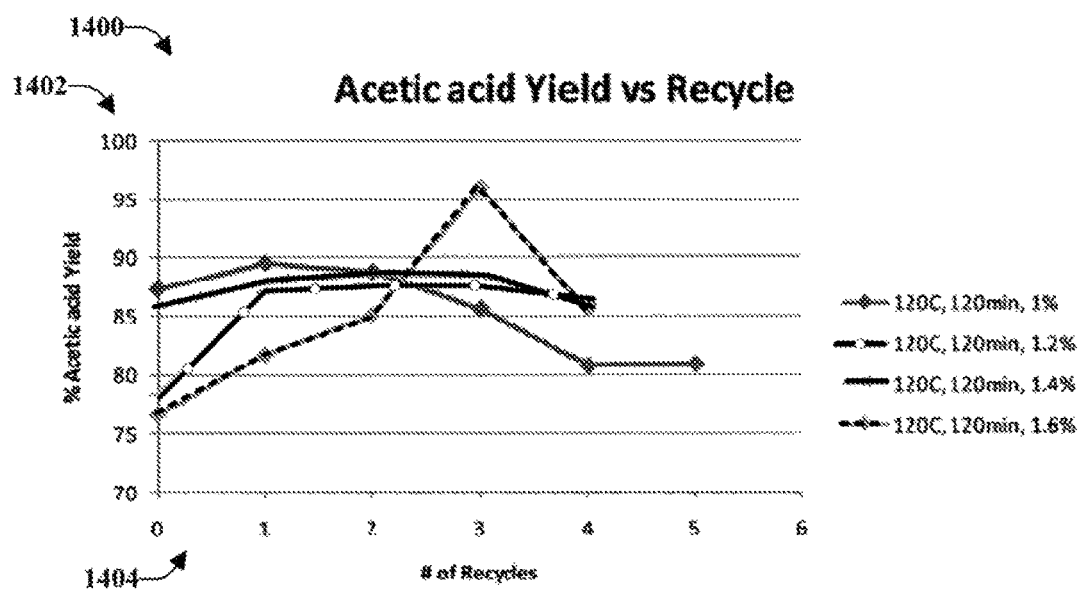
FIGS. 14-16 are example graphs of the acetic acid concentration in pretreated biomass as a function of recycle numbers for various process conditions, in accordance with some embodiments.
Figure 15:
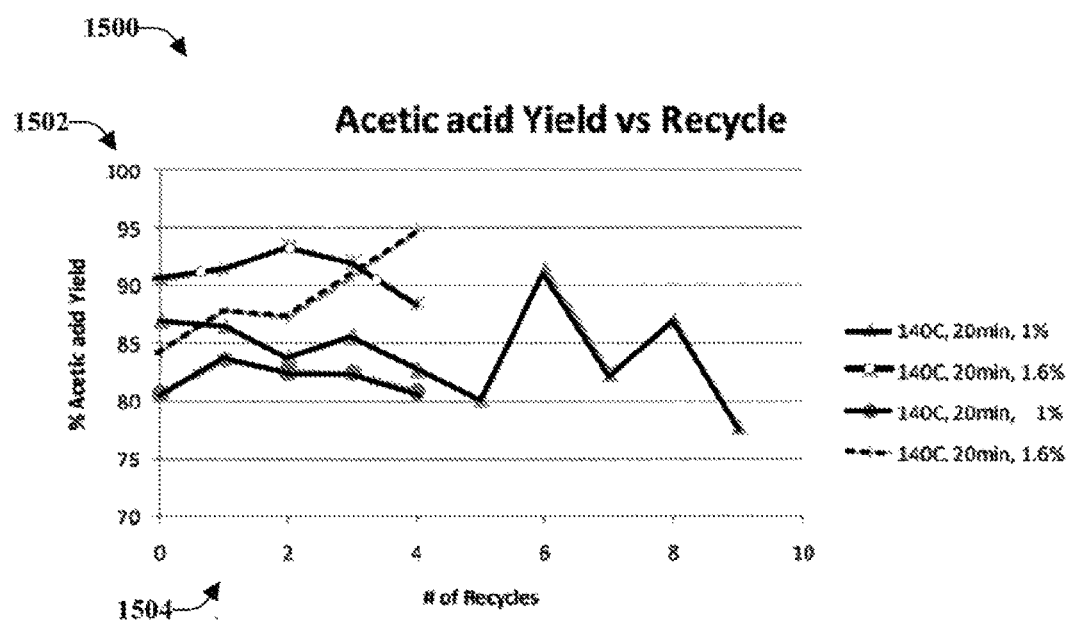
Figure 16:
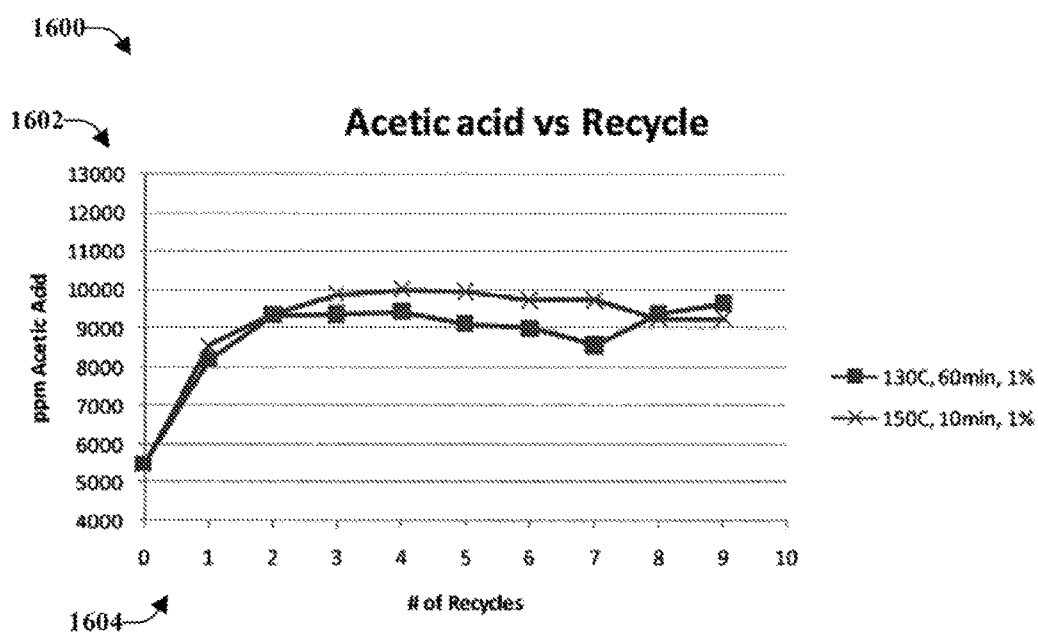

Results for the analysis of acetic acid as a function of number of recycles are illustrated in the graphs of FIGS. 14-16. In particular, FIG. 14 illustrates an example graph 1400 of percent acetic acid yields 1402 for the samples treated at 120° C. for 120 minutes at varying acid solutions as a function of recycle numbers 1404 (as detailed in FIG. 24). FIG. 15 illustrates an example graph 1500 of percent acetic acid yields 1502 for the samples treated at 140° C. for 20 minutes at varying acid solutions, as a function of recycle numbers 1504 (as detailed in FIG. 24). FIG. 16 illustrates an example graph 1600 of acetic acid concentrations 1602 for the samples treated at 150° C. for 10 minutes and 130° C. for 60 minutes, both with a 1% acid solution, as a function of recycle numbers 1604 (as detailed in FIG. 24). As illustrated, acetic acid concentrations increase as recycle numbers increase. Yields of acetic acid remain relatively consistent (as a percentage) over the successive recycles. Higher acid concentration tends to result in higher acetic acid formation, likely due to treatment severity.

Figure 17:
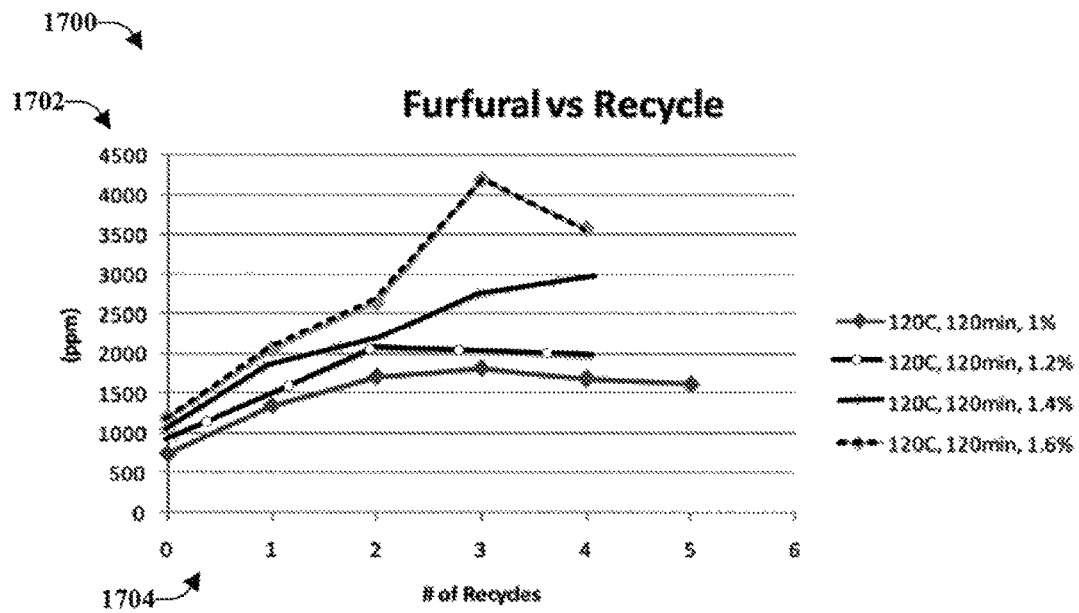
FIGS. 17-19 are example graphs of the furfural concentration in pretreated biomass as a function of recycle numbers for various process conditions, in accordance with some embodiments.
Figure 18:
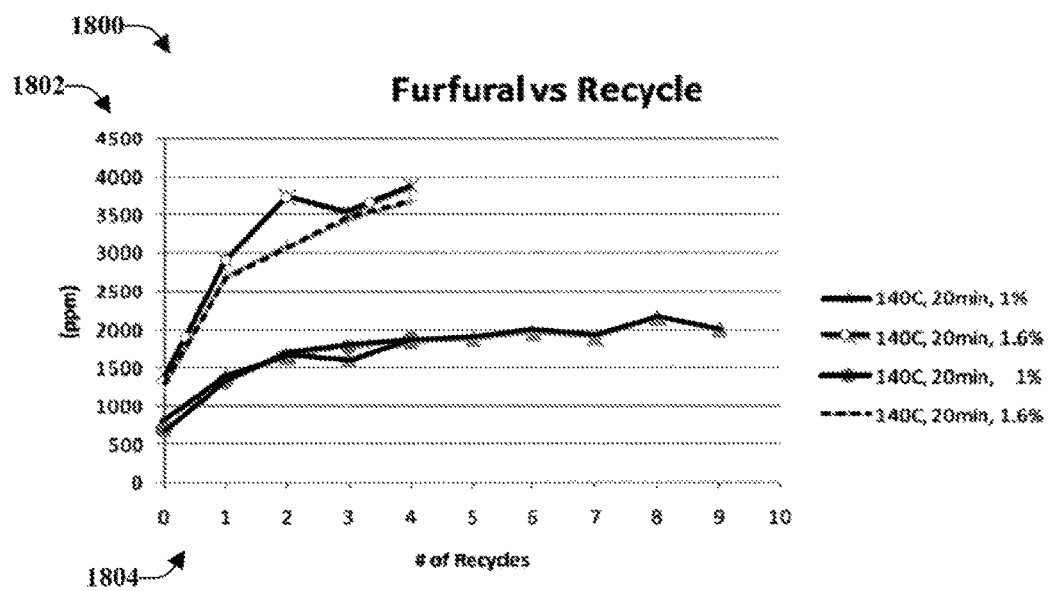
Figure 19:
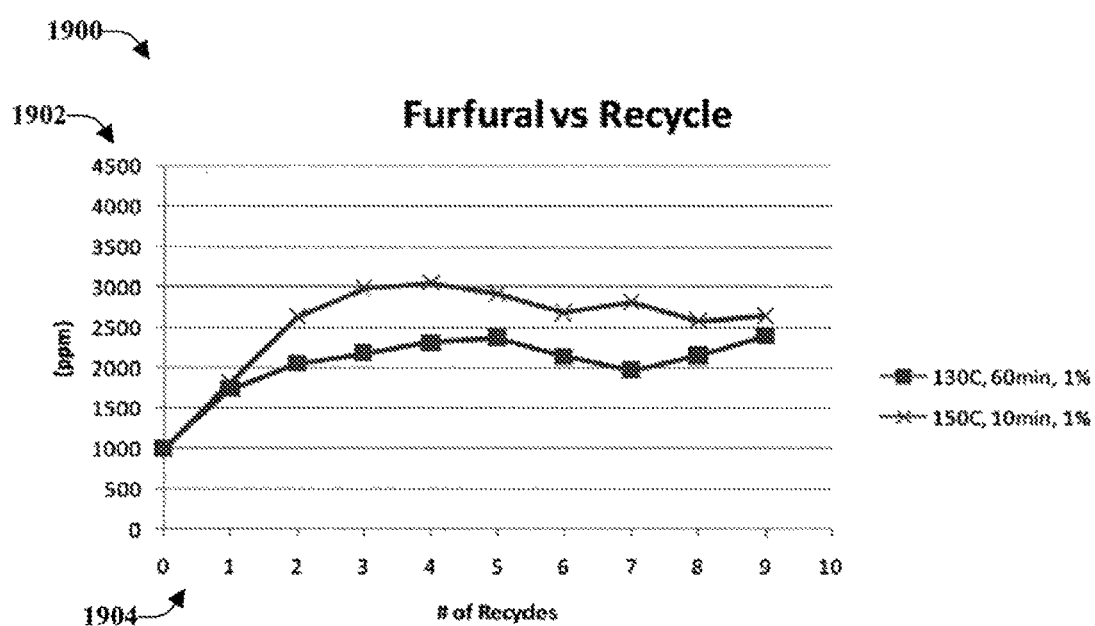

Results for the analysis of furfural as a function of number of recycles are illustrated in the graphs of FIGS. 17-19. In particular, FIG. 17 illustrates an example graph 1700 of furfural concentration 1702 for the samples treated at 120° C. for 120 minutes at varying acid solutions as a function of recycle numbers 1704 (as detailed in FIG. 24). FIG. 18 illustrates an example graph 1800 of percent furfural concentration 1802 for the samples treated at 140° C. for 20 minutes at varying acid solutions as a function of recycle number 1804 (as detailed in FIG. 24). FIG. 19 illustrates an example graph 1900 of furfural concentration 1902 for the samples treated at 150° C. for 10 minutes and 130° C. for 60 minutes, both with a 1% acid solution as a function of recycle numbers 1904 (as detailed in FIG. 24). As illustrated, furfural concentrations increase with each recycle at all conditions. Further, the level of furfural is much higher for the 1.6% acid compared to the 1% acid loading. The decreasing yields at 1% acid and the increasing yields at 1.6% acid tend to indicate a decreasing severity in the pretreatment as the xylose liquor is recycled at 1% acid and an increasing severity at 1.6% acid. This is likely a result of the slightly higher acetic acid being produced and the elevated levels of acid catalyst.

FIG. 25 summarizes the experimental data in tabular format. The 1% acid, 120° C., 2 hour xylose liquor recycle pretreatments resulted in xylose yields of 85-100% and glucose yields of 45-55% (from low enzyme dosing). When a 1.2% sulfuric acid was used the highest xylose yields occurred. In contrast, 1% acid yielded the highest glucose levels. Xylose yields between 90 and 100% are achieved with 1.6% acid loading. Acetic acid yields show the same trends for the 1% acid pretreatments at around 80-85% and the 1.6% acid pretreatments from 85-95% as compared to xylose yields. Glucose yields are between 45% and 65% with the 1.6% acid loading showing an upward trend over the 5 pretreatment cycles increasing from about 55-65% while the 1% actually seems to cause a decrease in glucose yield as it is recycled.

The 150° C. xylose liquor recycle pretreatments have xylose yields approaching 100% and glucose yields that start near 60% but then fall off to reach a steady state in the 50% range, the pretreatment also produces around 85-90% of the theoretical acetic acid available.

The 130° C. pretreatments have xylose yields in the 90-95% range that shows a decreasing yield as recycles progress, the same trend is seen in the acetic acid yield. The elevation in temperature from 130° C. to 150° C. causes an increased amount of xylose being converted to furfural. These trends in sugar, acetic acid, and furfural production support the assessment that 150° C. at the same acid level provides higher pretreatment severity than 130° C. for longer periods of time (10 minutes versus 60 minutes).

When the xylose yield trends are examined across the entire experimental design, the 1% acid recycles have a downward trend suggesting that there is not enough acid being recycled with the xylose liquor to maintain the severity level. Conversely, the 1.6% acid data shows an increase in both xylose and glucose yield which indicates that there is an increase in severity that leads to a higher yield pretreatment, possibly due to increasing levels of acetic acid. The 1.2% and 1.4% acid yield for xylose and glucose remain relatively steady.

The embodiments as disclosed and described in the application (including the FIGURES and Examples) are intended to be illustrative and explanatory of the present inventions. Modifications and variations of the disclosed embodiments, for example, of the apparatus and processes employed (or to be employed) as well as of the compositions and treatments used (or to be used), are possible; all such modifications and variations are intended to be within the scope of the present inventions.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

What is claimed is:

1. A method for pretreating lignocellulosic biomass, comprising:
    a) applying an acid solution to a first portion of biomass feedstock, wherein the biomass feedstock comprises ground corn cobs and corn stover, and wherein the acid solution comprises between about 1% to 1.6% sulfuric acid;
    b) maintaining an elevated temperature of the first portion of biomass feedstock to hydrolyze hemicellulose present in the biomass feedstock such that a xylose yield of greater than about 80% of theoretical is achieved, wherein a liquid xylose liquor comprising furfural in an amount of 4000 ppm or less and a glucan solid are produced from the first portion of biomass feedstock while maintaining the elevated temperature, wherein the maintaining the elevated temperature comprises maintaining the elevated temperature within the range of about 120° C. to 150° C.;
    c) before step "h", separating at least a portion of the liquid xylose liquor from the glucan solid;
    d) recycling a fraction of liquid xylose liquor that is separated from the glucan solid and applying the fraction of the liquid xylose liquor to a subsequent portion of the biomass feedstock, wherein the fraction of the liquid xylose liquor that is recycled is 70% or more of the total xylose liquor that is separated from the glucan solid;
    e) applying a makeup acid solution to the subsequent portion of the biomass feedstock;
    f) maintaining an elevated temperature of the subsequent portion of the biomass feedstock such that xylose yield of greater than about 80% of theoretical is achieved, wherein a liquid xylose liquor and a glucan solid are produced from the subsequent portion of the biomass feedstock while maintaining the elevated temperature, wherein the maintaining the elevated temperature comprises maintaining the elevated temperature within the range of about 120° C. to 150° C.;
    g) repeating steps c) through f) at least three times; and
    h) enzymatically hydrolyzing the glucan solid to produce glucose.

2. The method of claim 1, further comprising releasing sugar glucose.

3. The method of claim 2, wherein at step b) and step f) greater than about 45% of theoretical glucose yield is achieved.

4. The method of claim 2, wherein at step b) and step f) greater than about 50% of theoretical glucose yield is achieved.

5. The method of claim 1, wherein the maintaining the elevated temperature comprises maintaining the elevated temperature for at least about 10 minutes.

6. The method of claim 1, wherein the maintaining the elevated temperature comprises maintaining the elevated temperature for less than about 120 minutes.

7. The method of claim 1, wherein at step b) and step f) greater than about 90% of theoretical xylose yield is achieved.

8. The method of claim 1, wherein the liquid xylose liquor comprises less than about 3000 ppm furfural.

9. The method of claim 1, wherein step g) is repeated at least five times.

10. The method of claim 1, wherein step g) is repeated for about ten cycles.

11. A method for pretreating lignocellulosic biomass to be supplied to a fermentation system for production of a fermentation product, comprising:
    a) applying a xylose liquor to biomass feedstock, wherein the biomass feedstock comprises ground corn cobs and corn stover;
    b) applying a makeup acid solution to the biomass feedstock;
    c) maintaining an elevated temperature of the biomass feedstock to hydrolyze hemicellulose present in the biomass feedstock such that a xylose yield of greater than about 80% of theoretical is achieved, wherein xylose liquor comprising furfural in an amount of 4000 ppm or less and a glucan solid are produced from the biomass feedstock while maintaining the elevated temperature, wherein the maintaining the elevated temperature comprises maintaining the elevated temperature within the range of about 120° C. to 150° C.;
    d) before step "f", separating at least some portion of the xylose liquor from the glucan solid, and recycling a fraction of liquid xylose liquor that is separated from the glucan solid and applying the fraction of the liquid xylose liquor to a subsequent portion of the biomass feedstock, wherein the fraction of the liquid xylose liquor that is recycled is 70% or more of the total xylose liquor that is separated from the glucan solid;
    e) repeating steps a) through d) at least three times; and
    f) enzymatically hydrolyzing the glucan solid.

* * * * *